(12) United States Patent
Kim et al.

(10) Patent No.: US 9,090,608 B2
(45) Date of Patent: Jul. 28, 2015

(54) PHARMACEUTICAL COMPOSITION FOR PREVENTING OR TREATING OSTEOPOROSIS OR OBESITY COMPRISING PHENYLTETRAZOLE DERIVATIVE

(71) Applicant: KOREA RESEARCH INSTITUTE OF CHEMICAL TECHNOLOGY, Daejeon (KR)

(72) Inventors: Nak Jeong Kim, Daejeon (KR); Myung-Ae Bae, Daejeon (KR); Sung-Eun Yoo, Gongju-si (KR); Namsook Kang, Daejeon (KR); Jung Nyoung Heo, Daejeon (KR); Kyu Yang Yi, Daejeon (KR); Jee Hee Suh, Daejeon (KR); Sung Youn Chang, Daejeon (KR); Eun Sook Hwang, Seoul (KR); Jeong-Ho Hong, Seoul (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 13/734,348

(22) Filed: Jan. 4, 2013

(65) Prior Publication Data
US 2013/0123297 A1    May 16, 2013

Related U.S. Application Data

(62) Division of application No. 12/765,363, filed on Apr. 22, 2010, now Pat. No. 8,372,862.

(30) Foreign Application Priority Data

Jun. 2, 2009   (KR) .................. 10-2009-0048640
Dec. 8, 2009   (KR) .................. 10-2009-0121291

(51) Int. Cl.
*A61K 31/44* (2006.01)
*A61K 31/415* (2006.01)
*C07D 471/02* (2006.01)
(Continued)

(52) U.S. Cl.
CPC ............ *C07D 471/04* (2013.01); *A61K 31/437* (2013.01); *C07D 403/10* (2013.01)

(58) Field of Classification Search
CPC .... A61K 31/44; C07D 471/02; C07D 491/02; C07D 498/02; C07D 513/02; C07D 515/02
See application file for complete search history.

(56) References Cited

U.S. PATENT DOCUMENTS 5,194,379 A * 3/1993 Chen et al. .................... 435/119
5,250,554 A * 10/1993 Naka et al. .................... 514/381

(Continued)

FOREIGN PATENT DOCUMENTS

JP    3095181 A    4/1991
JP    7508028 A    9/1995
(Continued)

OTHER PUBLICATIONS

Freshney, RI. Culture of Animal Cells: A Manual of Basic Technique. John Wiley and Sons. 2005, 5th Ed., p. 8.*
(Continued)

*Primary Examiner* — Rita Desai
*Assistant Examiner* — Ben S Michelson
(74) *Attorney, Agent, or Firm* — Sughrue Mion, PLLC

(57) ABSTRACT

A pharmaceutical composition comprising a phenyltetrazole derivative of formula (I) or a pharmaceutical acceptable salt thereof is effective in preventing or treating osteoporosis, obesity, diabetes, or hyperlipidemia, by regulating protein TAZ.

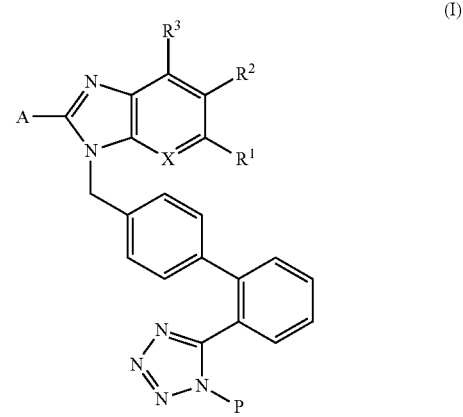

wherein, A is ethyl or n-butyl; $R^1$ is methyl, —$CH_2OH$, —$CO_2CH_3$, —$CH_2F$, —$CH(OCH_3)_2$, —$CH_2OC(=O)CH_3$, styryl or —$CH_2OCH_2SCH_3$; $R^2$ is H, Br, —$CO_2CH_3$, phenyl, pyridin-2-yl, pyridin-3-yl,

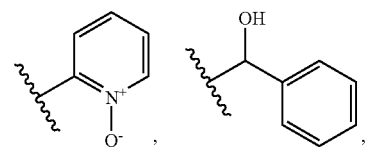

or styryl; $R^3$ is H or methyl; X is CH or N; and P is H or —$CH(CH_3)OCH_2CH_3$.

2 Claims, No Drawings

(51) Int. Cl.

| | |
|---|---|
| C07D 491/02 | (2006.01) |
| C07D 498/02 | (2006.01) |
| C07D 513/02 | (2006.01) |
| C07D 515/02 | (2006.01) |
| C07D 403/02 | (2006.01) |
| C07D 235/04 | (2006.01) |
| C07D 471/04 | (2006.01) |
| A61K 31/437 | (2006.01) |
| C07D 403/10 | (2006.01) |

(56) References Cited

U.S. PATENT DOCUMENTS

| | | | | |
|---|---|---|---|---|
| 5,332,744 | A | * | 7/1994 | Chakravarty et al. ...... 514/263.2 |
| 5,661,158 | A | * | 8/1997 | Ohtsuka et al. ............... 514/312 |
| 5,691,348 | A | * | 11/1997 | Yoo et al. ...................... 514/300 |
| 5,849,753 | A | | 12/1998 | Yoo et al. |

FOREIGN PATENT DOCUMENTS

| | | |
|---|---|---|
| JP | 9507675 A | 8/1997 |
| WO | 9323399 A1 | 11/1993 |
| WO | 9521838 A1 | 8/1995 |
| WO | 95/34564 A1 | 12/1995 |
| WO | 2005/023182 A2 | 3/2005 |
| WO | 2006/093864 A1 | 9/2006 |
| WO | 2006/099058 A2 | 9/2006 |
| WO | 2007/019448 A2 | 2/2007 |

OTHER PUBLICATIONS

Hong, JH. et al. TAZ, a Transcriptional Modulator of Mesenchymal Stem Cell Differentiation. Science. 2005, vol. 309, p. 1076.*
Lei, QY. et al. TAZ promotes Cell Proliferation and Epithelial-Mesenchymal Transition and Is inhibited by the Hippo Pathway. Molecular and Cellular Biology. 2008, vol. 28, p. 2427, results, line 8.*
Cornelison, TL. Human papillomavirus genotype 16 vaccines for cervical cancer prophylaxis and treatment. Curr. Opin. Oncol. 2000, vol. 12(5), p. 466.*
Yoo, S. et al. A Comparative Molecular Field Analysis and Molecular Modelling Studies on Pyridylimidazole Type of Angiotensin II Antagonists. Bioorganic & Medicinal Chemistry. 1999, vol. 7, p. 2972.*
Shimizu, H. et al. Angiotensin II accelerates osteoporosis by activating osteoclasts. The FASEB Journal. 2008, vol. 22, p. 2474.*
Chinese Patent Office, Chinese Office Action issued in corresponding CN Application No. 201010190815.2, dated Aug. 12, 2011.
Yoo et al., "A Comparative Molecular Field Analysis and Molecular Modeling Studies on Pyridylimidazole Type of Angiotensin II Antagonists," Bioorganic & Medicinal Chemistry, 1999, vol. 7, pp. 2971-2976.
Japanese Patent Office, Office Action dated Oct. 16, 2012, issued in corresponding Japanese Patent Application No. 3-095181.
Gulcan et al., "Are there any effects of angiotensin II receptor blockers on postmenopausal osteoporosis?" Medical Hypothesis, 2008, pp. 701-702, vol. 70(3).
Huang et al., "Pancreatic Islet Blood Flow is Selectively Enhanced by Captopril, Irbesartan and Pravastatin, and Suppressed by Palmitate" Biochemical and BioPhysycal Research Communications, 2006, pp. 26-32, vol. 346.
Jones et al., "Angiotensin II Increases Lipogenesis in 3T3-L1 and Human Adipose Cells" Endocrinology, 1997, pp. 1512-1519, vol. 138 No. 4.
Zober et al., "PET Imaging of the AT, Receptor with [$^{11}$C]KR31173," Nuclear Medicine and Biology, 2006, vol. 33, pp. 5-13.
Jang et al. "TM-25659 enhances osteogenix differentiation and suppresses adipogenic differentiation by modulating the transcriptional co-activator TAZ" British Journal of Pharmacology (2012), pp. 1584-1594, vol. 165.

* cited by examiner

12# PHARMACEUTICAL COMPOSITION FOR PREVENTING OR TREATING OSTEOPOROSIS OR OBESITY COMPRISING PHENYLTETRAZOLE DERIVATIVE

CROSS-REFERENCE TO RELATED APPLICATIONS

This application is a divisional of U.S. application Ser. No. 12/765,363 filed Apr. 22, 2010 (U.S. Pat. No. 8,372,862), which claims priority based on Korean Patent Application No. 10-2009-0048640 filed Jun. 2, 2009 and Korean Patent Application No. 10-2009-0121291 filed Dec. 8, 2009, the contents of all of which are incorporated herein by reference in their entirety.

FIELD OF THE INVENTION

The present invention relates to a pharmaceutical composition for preventing or treating osteoporosis, obesity, diabetes, or hyperlipidemia, comprising a phenyltetrazole derivative or a pharmaceutical acceptable salt thereof as an active ingredient.

BACKGROUND OF THE INVENTION

Senile diseases such as osteoporosis are becoming preponderant with an ever increasing number of the elderly people. Osteoporosis is a bone disease that causes reduced bone mineral density (BMD), disrupted bone microarchitecture, and alteration of the amounts various proteins in bone, leading to an increased risk of fracture. Osteoporosis is caused by an imbalance between bone resorption and bone formation and progresses when bone resorption outpaces bone formation. With osteoporosis, the calcified bone tissue density decreases, causing the expansion of marrow cavity. As the symptoms progress, bone fracture occurs easily even by a slight stressful impact.

Early studies for osteoporosis had focused mainly on calcium and phosphorus metabolic disorders, but failed to define the pathogenesis thereof. The existing therapeutic agents for treating osteoporosis are represented by bisphosphonate products (e.g., Alendronate and Etidronate), hormone products (e.g., raloxifene), vitamin D products, calcitonin products, and calcium products. However, bisphosphonate products have the problems of a low absorption rate, a complicated method of administration, and the tendency to induce esophagitis. Hormone products require life-time administration, which may cause side effects such as breast cancer, uterine cancer, cholelithiasis, and thrombosis. Vitamin D products are expensive but not much effective. Calcitonin products have also the problems of high costs and an uneasy method of administration. Calcium products have fewer side effects but are limited to prevention rather than treatment. Short-term administration of a drug is not much effective for the treatment of osteoporosis, requiring long-term administration of a drug. Therefore, a novel drug causing much reduced side effects and having enhanced medicinal effects is required for long-term administration.

Bone marrow-derived adult stem cells, particularly mesenchymal stem cells (MSCs), are of a pluripotent cell type that differentiates into several distinct cell lineages, such as osteocytes, chondrocytes, myocytes, and adipocytes. The differentiation of adult stem cells tends to reduce the age-related diseases, to prevent: the reduction in the regeneration of bone, cartilage, and muscle tissues; the decline of the immune function; and environment-caused diseases. Thus, a method for activating the differentiation of adult stem cells may be an efficacious therapy for diseases associated with metabolic diseases, bone diseases, and aging.

The differentiation of adult stem cells into a specific cell type is controlled by an important transcription factor, the expression of which is regulated by the interaction with the outer signal transduction. In particular, adipocyte differentiation is known to be regulated by transcription factor PPARγ (peroxisome proliferation-activated receptor γ). The transcription factor facilitates or inhibits the adipocyte differentiation by binding with different ligands, and an increase in the activity of the transcription factor is known to facilitate the adipocyte differentiation, leading to increased obesity [MacDougald et al., Annu. Rev. Biochem., 1995; 64:345-73; Adams et al., J. Clin. Invest., 1997; 100:3149-53; Fajas et al., Curr. Opin. Cell Biol., 1998; 10:165-73].

Recently, a transcription coactivator, protein TAZ (transcription coactivator with PDZ-binding motif), which regulates the transcription factor PPAR γ has been identified [Kanai et al., Embo. J., 2000; 19:6778-91].. The TAZ protein is cloned as a partner protein which binds to 14-3-3 proteins, and it is phosphorylated at serine 89, which interact with 14-3-3 proteins in the cytosol [Kanai et al., Embo. J., 2000; 19:6778-91; Park et al., J. Biol. Chem., 2004; 279:17384-90]. The TAZ protein contains WW domains, coiled-coil domains, and PDZ-binding motifs, which suggests the possibility of various binding with other proteins. In particular, the WW domains show strong binding affinity with peptide sequence PPXY, which suggests the possibility of the TAZ protein to bind with several proteins containing PPXY motifs. In 2003, it was found that the WW domains in protein TAZ bind with RUNX2 (runt-related transcription factor 2) which is a decisive regulatory factor to facilitate the osteoclast differentiation. It was reported that the expression regulatory activity of RUNX2 target gene is amplified and the expression of bone-specific gene increases, leading to an osteogenic facilitation, through the binding [Hong et al., Science, 2005; 309: 1074-8]. Further, polymavirus T antigen, a protein binding to the WW domains in protein TAZ is known, but its precise function in cells is not clearly understood. Furthermore, PPARγ, one of transcription factor having PPXY motif, has been identified as a novel TAZ binding protein, and such binding inhibits the adipocyte differentiation by PPARγ [Hong et al., Science, 2005; 309:1074-8]. The mechanism of protein TAZ for the inhibition of adipocyte differentiation is explained by the fact that protein TAZ binds with PPARγ not only to inhibit the DNA binding activity of PPARγ but also to inhibit the gene transcription facilitation activity, thus inhibiting the expression of adipocyte-specific PPARγ target gene. The binding of protein TAZ with RUNX2 and PPARγ plays a significant important role in regulating the differentiation of MSCs. Specifically, it has been found in the differentiation of MSCs that osteoclasts differentiation is facilitated, while the adipocyte differentiation is regressed by the binding of protein TAZ with proteins RUNX2 and PPARγ, [Hong et al., Science, 2005; 309:1074-8; Deng et al., Front Biosci., 2008; 13:2001-21; Hong et al., Cell Cycle 2006; 5:176-179]. That is, the differentiation of protein TAZ determines the differentiation of MSCs.

TBX5 (T-box transcription factor 5) is known as another TAZ binding protein, and the binding thereof is understood to play an important role in the limb and cardiac formation [Murakami et al., Proc. Natl. Acad. Sci., USA., 2005; 102: 18034-9]. Further, TBX5 possibly binds with protein PAX3 important in the early embryonic phase to regulate its function [Murakami et al., Biochemical & Biophysical Research Communications, 2006; 339:533-9]. In addition, protein TAZ shows its activity by binding with various PDZ domain-containing proteins through PDZ-binding motif. TTF-1 (thyroid transcription factor-1) is a gene that plays an active role in the lung development, and regulates the surfactant protein-C gene expression. Protein TAZ is considered to be a transcription coactivator that facilitates the surfactant protein-C gene expression by binding with TTF-1 [Park et al., J. Biol. Chem., 2004; 279:17384-90]. Further, protein TAZ is suggested to regulate the expression of TEF-1 regulatory genes in muscle tissues by binding with TEF-1 (transcription enhancer factor-1) [Mahoney et al., Biochem. J., 2005; 388:217-25].

Aside from the TAZ function of modulating mesenchymal stem cell differentiation, other functions thereof in the migration, invasion, and tumorigenesis of breast cancer cells MCF7 are known [Chan et al., Cancer Res., 2008; 68:2592-8]. The occurrence of polycystic kidney disease which forms multiple renal cysts has been reported in TAZ-deficient animal models, and various approaches for the functions of protein TAZ have been attempted [Makita et al., Am. J. Physiol. Renal. Physiol., 2008; 294:F542-53; Tian et al., Molecular & Cellular Biology, 2007; 27:6383-95]. Meanwhile, there have been some reports that FGF-2 causes the decrease of the TAZ protein in osteogenic differentiation [Deng Z L et al., Front Biosci., 2008; 13:2001-21; Eda et al., Biochemical & Biophysical Research Communications, 2008; 366:471-5], but few investigations on the regulatory mechanism of the TAZ protein have been conducted despite the importance of functions of the TAZ protein.

In case of the TAZ protein which acts as a transcription co-activator to regulate transcription factors with DNA binding activity, the migration thereof from cytosol to nucleus is prerequisite. Until now, it is known that the TAZ protein can migrate into the nucleus by serine dephosphorylation, and the inhibition of binding between proteins TAZ and 14-3-3 is suggested as a method for increasing the migration of the TAZ protein into the nucleus. Thus, compounds which facilitate the migration of TAZ into the nucleus may be considered to have an inhibitory effect on the adipocyte differentiation and facilitates the osteoblast differentiation.

The present inventors have endeavored to seek out a compound effective for preventing or treating osteoporosis, diabetes, or hyperlipidemia, which has led the finding that phenyltetrazole derivatives are effective in the treatment or prevention of osteoporosis by regulating the TAZ protein and also in the treatment of the obesity by inhibiting adipocyte differentiation.

SUMMARY OF THE INVENTION

Accordingly, it is an object of the present invention to provide a pharmaceutical composition for preventing or treating osteoporosis, obesity, diabetes, or hyperlipidemia, comprising a phenyltetrazole derivative or a pharmaceutical acceptable salt thereof as an active ingredient.

In accordance with one aspect of the present invention, there is provided a pharmaceutical composition for preventing or treating osteoporosis, obesity, diabetes, or hyperlipidemia, comprising a compound of formula (I) or a pharmaceutical acceptable salt thereof as an active ingredient:

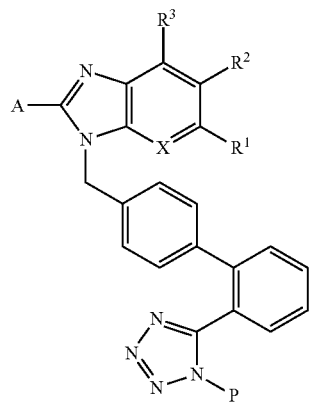

(I)

wherein, A is ethyl or n-butyl; $R^1$ is methyl, —$CH_2OH$, —$CO_2CH_3$, —$CH_2F$, —$CH(OCH_3)_2$, —$CH_2OC(=O)CH_3$, styryl or —$CH_2OCH_2SCH_3$; $R^2$ is H, Br, —$CO_2CH_3$, phenyl, pyridin-2-yl, pyridin-3-yl,

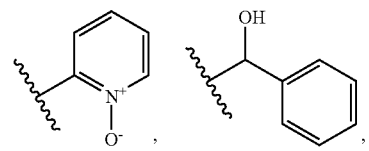 [SMILES: *c1cccc[n+]1[O-] ; *C(O)c1ccccc1]

or styryl; $R^3$ is H or methyl; X is CH or N; and P is H or —$CH(CH_3)OCH_2CH_3$.

The inventive pharmaceutical composition comprising phenyltetrazole derivatives of formula (I) is effective in preventing or treating osteoporosis, obesity, diabetes, or hyperlipidemia, by regulating protein TAZ.

DETAILED DESCRIPTION OF THE INVENTION

Hereinafter, the pharmaceutical composition according to the present invention is described in detail.

The compound of formula (I) is preferably selected from the group consisting of:
{2-ethyl-7-methyl-3-[2'-(1H-tetrazol-5-yl)biphenyl-4-ylmethyl]-3H-imidazo [4,5-b]pyridin-5-yl}methanol, represented by formula (II):

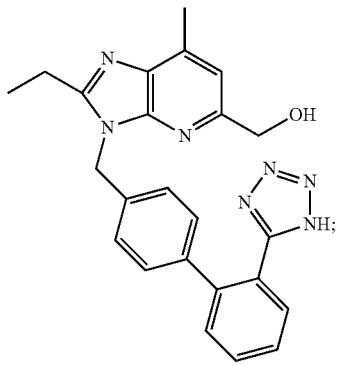

(II)

2-butyl-5-methyl-6-pyridin-3-yl-3-[2'-(1H-tetrazol-5-yl) biphenyl-4-ylmethyl]-3H-imidazo[4,5-b]pyridine, represented by formula (III):

(III)

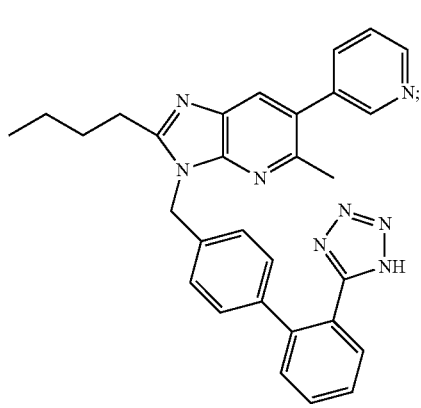

methyl 2-butyl-6-pyridin-2-yl-3-[2'-(1H-tetrazol-5-yl)biphenyl-4-ylmethyl]-3H-imidazo[4,5-b]pyridine-5-carboxylate, represented by formula (IV):

(IV)

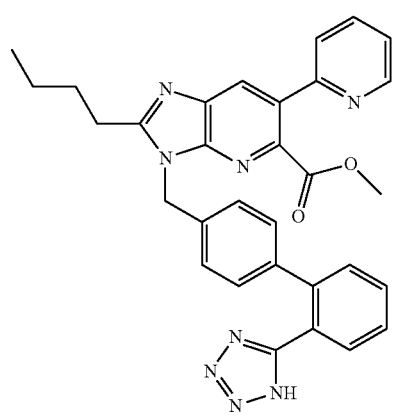

{2-butyl-7-methyl-3-[2'-(1H-tetrazol-5-yl)biphenyl-4-ylmethyl]-3H-imidazo[4,5-b]pyridin-5-yl}methanol, represented by formula (V):

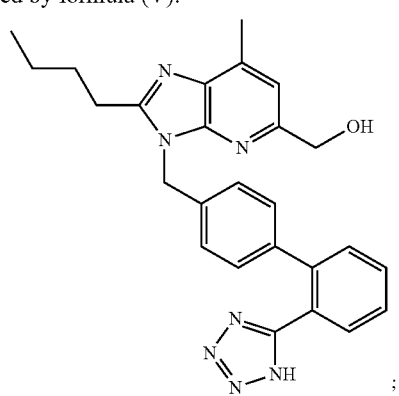

2-butyl-5-fluoromethyl-6-(1-oxypyridin-2-yl)-3-[2'-(1H-tetrazol-5-yl)biphenyl-4-ylmethyl]-3H-imidazo[4,5-b]pyridine, represented by formula (VI):

(VI)

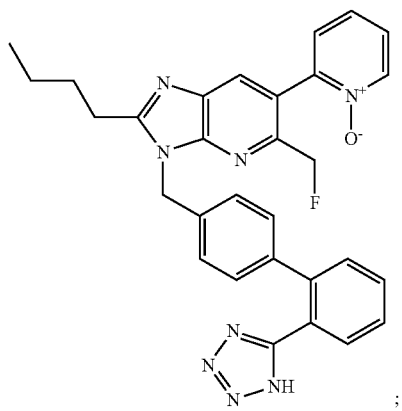

(2-butyl-5-dimethoxymethyl-3-{2'-[1-(1-ethoxyethyl)-1H-tetrazol-5-yl]biphenyl-4-ylmethyl}-3H-imidazo[4,5-b]pyridin-6-yl)phenylmethanol, represented by formula (VII):

(VII)

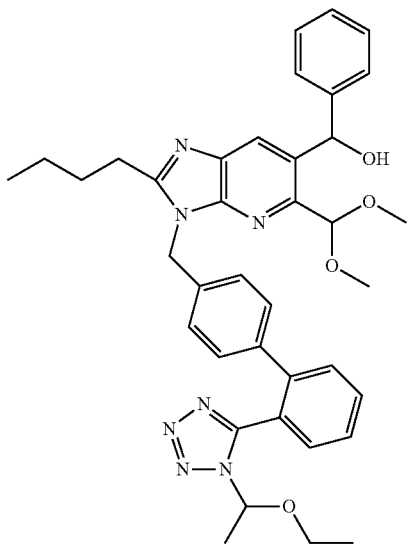

{2-butyl-5-dimethoxymethyl-3-[2'-(1H-tetrazol-5-yl)biphenyl-4-ylmethyl]-3H-imidazo[4,5-b]pyridin-6-yl}phenylmethanol, represented by formula (VIII):

(VIII)

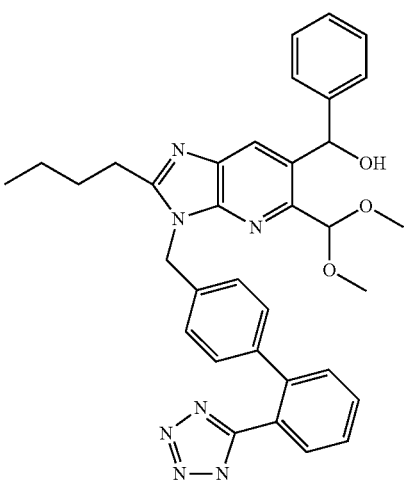

6-bromo-2-butyl-3-{2'-[1-(1-ethoxyethyl)-1H-tetrazol-5-yl]biphenyl-4-ylmethyl}-3H-imidazo[4,5-b]pyridin-5-ylmethyl acetate, represented by formula (IX):

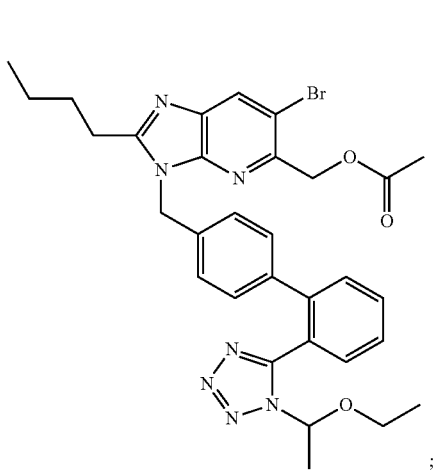

(IX)

6-bromo-2-butyl-3-[2'-(1H-tetrazol-5-yl)biphenyl-4-ylmethyl]-3H-imidazo[4,5-b]pyridin-5-ylmethyl acetate, represented by formula (X):

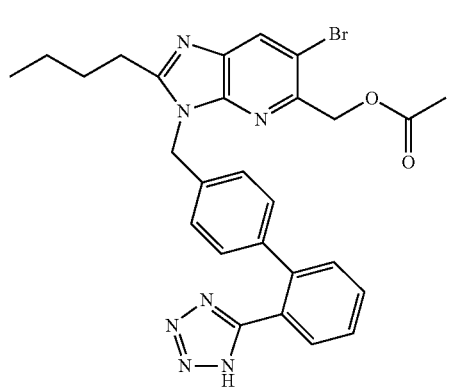

(X)

2-butyl-7-methyl-5-((methylsulfanylmethoxy)methyl)-6-phenyl-3-[2'-(1H-tetrazol-5-yl)biphenyl-4-ylmethyl]-3H-imidazo[4,5-b]pyridine, represented by formula (XI):

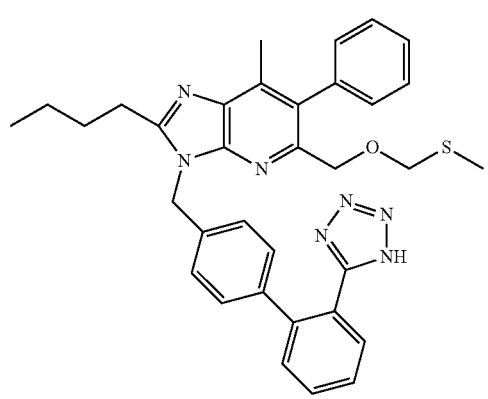

(XI)

methyl 2-butyl-6-styryl-1-[2'-(1H-tetrazol-5-yl)biphenyl-4-ylmethyl]-1H-benzimidazol-5-carboxylate, represented by formula (XII):

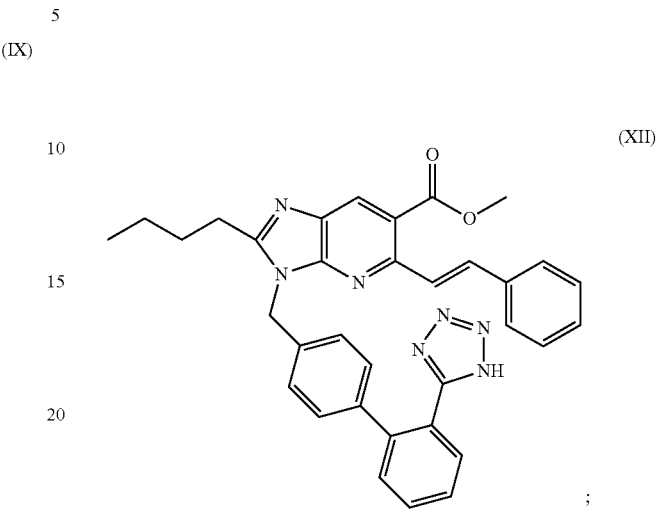

(XII)

methyl 2-butyl-5-styryl-1-[2'-(1H-tetrazol-5-yl)biphenyl-4-ylmethyl]-1H-benzimidazol-6-carboxylate represented by formula (XIII):

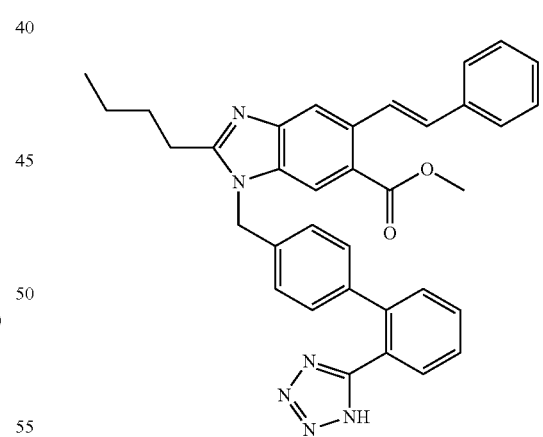

The compounds of formulas (II) to (XIII) are more explained as follows:

TABLE 1

Structures and characteristics of the compounds of the present invention

| Compound (formula) | Structure | References or ¹H-NMR data (ppm) |
|---|---|---|
| II | 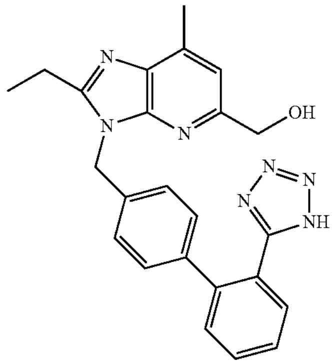 [SMILES: CCc1nc2c(C)cc(CO)nc2n1Cc1ccc(-c2ccccc2-c2nnn[nH]2)cc1] | U.S. Pat. No. 5,332,744; EP 400974; and WO 95/34564. |
| III | 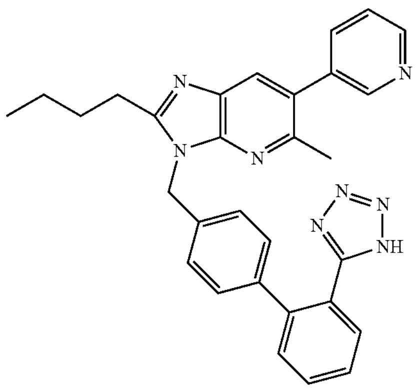 [SMILES: CCCCc1nc2cc(-c3cccnc3)c(C)nc2n1Cc1ccc(-c2ccccc2-c2nnn[nH]2)cc1] | WO 95/021838, WO 95/34564; KR Patent Publication No. 95-25039; U.S. Pat. No. 5,849,753; and Bioorg. Med. Chem., 7(12), 2971 (1999). |
| IV | 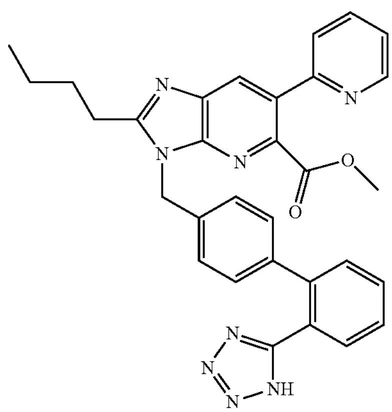 [SMILES: CCCCc1nc2cc(-c3ccccn3)c(C(=O)OC)nc2n1Cc1ccc(-c2ccccc2-c2nnn[nH]2)cc1] | WO 95/021838; KR Patent Publication No. 95-25039; U.S. Pat. No. 5,849,753; EP 0743943; Bioorg. Med. Chem., 7(12), 2971 (1999); and Chem. Med. Chem., 2(9), 1298-1310, (2007). |
| V | 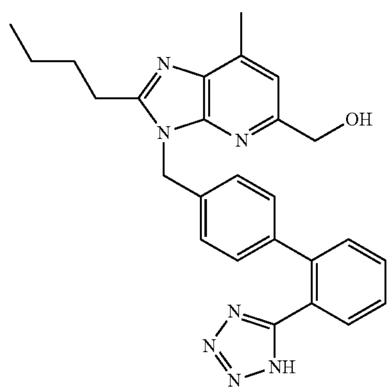 [SMILES: CCCCc1nc2c(C)cc(CO)nc2n1Cc1ccc(-c2ccccc2-c2nnn[nH]2)cc1] | U.S. Pat. No. 5,849,753; EP 0765328; WO 95/21838; and KR Patent Publication No. 95-25039. |

TABLE 1-continued

Structures and characteristics of the compounds of the present invention

| Compound (formula) | Structure | References or ¹H-NMR data (ppm) |
|---|---|---|
| VI | 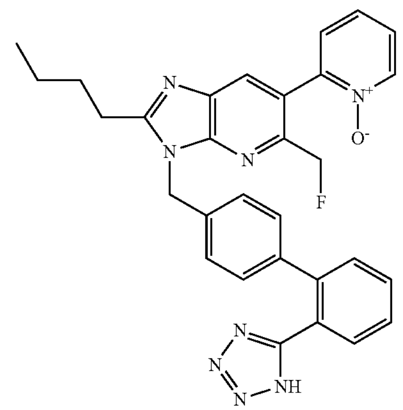 [SMILES: CCCCc1nc2cc(-c3cccc[n+]3[O-])c(CF)nc2n1Cc1ccc(-c2ccccc2-c2nnn[nH]2)cc1] | ¹H-NMR (300 MHz, CDCl₃) δ 0.78 (t, 3H), 1.29 (m, 2H), 1.60 (br-s, 2H), 2.66 (br-s, 2H), 5.10 and 5.45 (d, 2H), 5.60 (br-s, 2H), 6.73 (d, 2H), 6.95 (d, 2H), 7.15 (d, 1H), 7.39-7.48 (m, 5H), 7.48 (d, 1H), 7.75 (s, 1H), 8.38 (d, 1H) |
| VII | 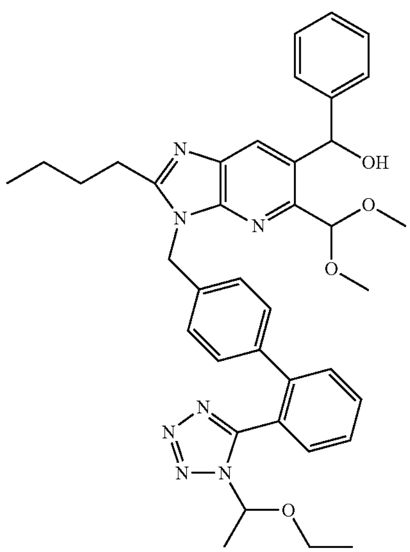 [SMILES: CCCCc1nc2cc(C(O)c3ccccc3)c(C(OC)OC)nc2n1Cc1ccc(-c2ccccc2-c2nnnn2C(C)OCC)cc1] | ¹H-NMR (300 MHz, CDCl₃) δ 0.90 (t, 3H), 1.07 (t, 3H), 1.38 (m, 2H). 1.65 (d, 3H), 1.77 (m, 2H), 2.74 (t, 2H), 3.22 (m, 1H), 3.43 (m, 1H), 3.49 (s, 3H), 3.59 (s, 3H), 3.67 (s, 1H), 5.47 (s, 2H), 5.52 (s, 1H), 5.88 (q, 1H), 6.77 (s, 1H), 7.11 (m, 4H), 7.39 (m, 3H), 7.50 (m 4H), 7.70 (s, 1H), 7.87 (d, 1H, J = 7.2 Hz) |
| VIII | 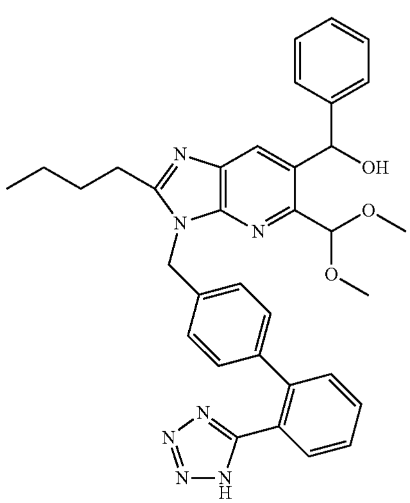 [SMILES: CCCCc1nc2cc(C(O)c3ccccc3)c(C(OC)OC)nc2n1Cc1ccc(-c2ccccc2-c2nnn[nH]2)cc1] | ¹H-NMR (300 MHz, CDCl₃) δ 0.85 (t, 3H), 1.31 (m, 2H), 1.65 (m, 2H), 2.63 (t, 2H), 3.41 (s, 3H), 3.50 (s, 3H), 5.38 (m, 2H), 5.54 (s, 1H), 6.64 (s, 1H), 6.97 (m, 4H), 7.36 (m, 3H), 7.41 (d, 2H, J = 7.1 Hz), 7.53 (m, 2H), 7.65 (s, 1H), 7.93 (d, 1H, J = 7.5 Hz) |

TABLE 1-continued

Structures and characteristics of the compounds of the present invention

| Compound (formula) | Structure | References or ¹H-NMR data (ppm) |
|---|---|---|
| IX | 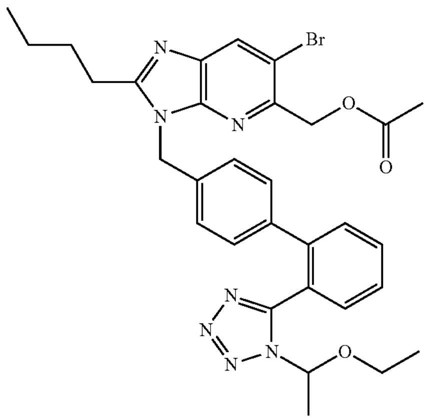 [SMILES: CCCCc1nc2cc(Br)c(COC(C)=O)nc2n1Cc1ccc(-c2ccccc2-c2nnnn2C(C)OCC)cc1] | ¹H-NMR (300 MHz, CDCl₃) δ 8.16 (s, 1H), 7.88 (dd, J = 7.5, 1.6 Hz, 1H), 7.50 (m, 2H), 7.41 (dd, J = 7.5, 1.6 Hz, 1H), 7.14 (d, J = 8.4 Hz, 2H), 7.08 (d, J = 8.4 Hz, 2H), 5.88 (q, 1H), 5.42 (m, 4H), 3.42 (m, 1H), 3.20 (m, 1H), 2.80 (t, 2H), 2.14 (s, 3H), 1.78 (m 2H), 1.63 (d, J = 6.0 Hz, 3H), 1.41 (m, 2H), 1.05 (t, 3H), 0.92 (t, 3H). |
| X | 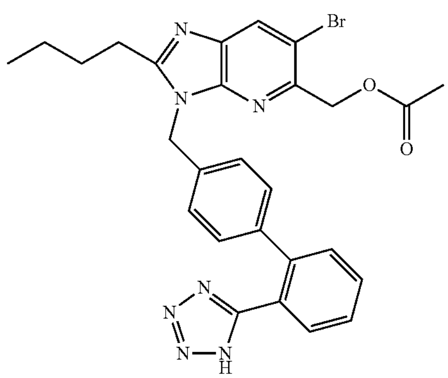 [SMILES: CCCCc1nc2cc(Br)c(COC(C)=O)nc2n1Cc1ccc(-c2ccccc2-c2nnn[nH]2)cc1] | ¹H-NMR (300 MHz, CDCl₃) δ 7.98 (d, J = 7.3 Hz, 1H), 7.58-7.67 (m, 3H), 7.42 (d, J = 7.3 Hz, 1H), 7.03 (d, J = 6.8 Hz, 2H), 6.94 (d, J = 6.8 Hz, 2H), 5.41 (s, 2H), 5.36 (s, 2H), 2.73 (t, 2H), 2.10 (s, 3H), 1.69 (m, 2H), 1.35 (m, 2H), 0.89 (t, 2H). |
| XI | 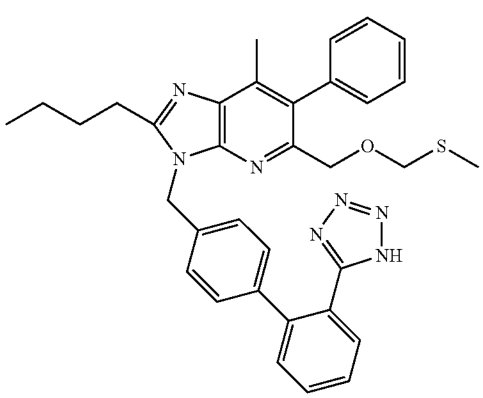 [SMILES: CCCCc1nc2c(C)c(-c3ccccc3)c(COCSC)nc2n1Cc1ccc(-c2ccccc2-c2nnn[nH]2)cc1] | ¹H NMR (300 MHz, CDCl₃) δ 0.95 (t, 3H), 1.43 (m, 2H), 1.80 (m, 2H), 2.07 (s, 3H), 2.35 (s, 3H), 2.85 (t, 2H), 4.55 (s, 2H), 4.85 (s, 2H), 5.30 (s, 2H), 7.00 (m, 4H), 7.20 (m, 2H), 7.32 (m, 2H) 7.45 (m, 5H) |

TABLE 1-continued

Structures and characteristics of the compounds of the present invention

| Compound (formula) | Structure | References or ¹H-NMR data (ppm) |
|---|---|---|
| XII | 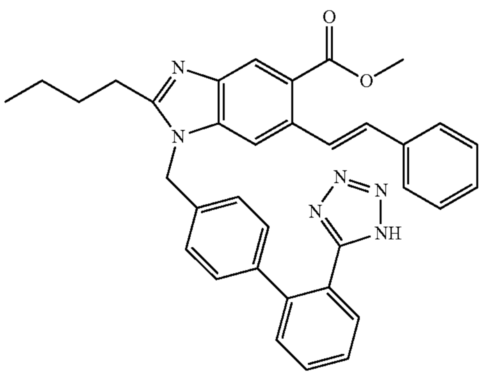 [SMILES: CCCCc1nc2cc(C(=O)OC)c(/C=C/c3ccccc3)cc2n1Cc1ccc(-c2ccccc2-c2nnn[nH]2)cc1] | ¹H-NMR (300 MHz, CDCl₃) δ 0.83 (t, 3H), 1.29 (m, 2H), 1.59 (m, 2H), 2.41 (t, 2H), 3.89 (s, 3H), 5.29 (s, 2H), 6.71 (d, 2H, J = 8.1 Hz), 6.76 (d, 1H, J = 16.1 Hz), 6.91 (d, 2H, J = 8.1 Hz), 7.23-7.32 (m, 5H), 7.37 (s, 1H), 7.47 (s, 1H), 7.49 (m, 1H), 7.54-7.65 (m, 2H), 7.90 (d, 1H, J = 16.1 Hz), 8.00 (dd, 1H) |
| XIII | 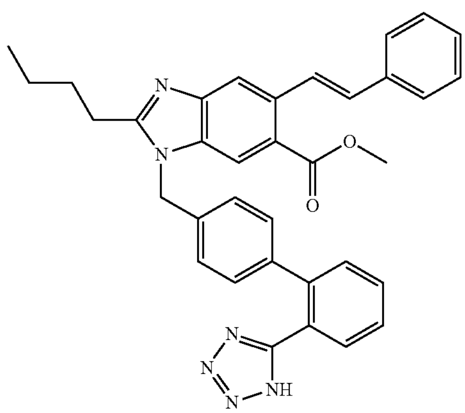 [SMILES: CCCCc1nc2cc(/C=C/c3ccccc3)c(C(=O)OC)cc2n1Cc1ccc(-c2ccccc2-c2nnn[nH]2)cc1] | ¹H-NMR (300 MHz, CDCl₃) δ 0.86 (t, 3H), 1.30 (m, 2H), 1.62 (m, 2H), 2.44 (t, 2H), 3.88 (s, 3H), 5.26 (s, 2H), 6.62 (d, 1H, J = 16.0 Hz), 6.71 (d, 2H, J = 8.1 Hz), 6.92 (d, 2H, J = 8.1 Hz), 7.14 (s, 1H), 7.29-7.34 (m, 2H), 7.37-7.43 (m, 2H), 7.49-7.55 (m, 4H), 7.62 (s, 1H), 7.85 (d, 1H, J = 16.0 Hz), 7.98 (m, 1H) |

The compounds of formulas (II) to (V) can be prepared by the methods according to the conventional methods. Hereinafter, the preparation methods of the compounds of formulas (VI) to (XIII) are described in detail.

The compound of formula (VI) may be prepared according to Reaction Scheme 1:

Reaction Scheme 1

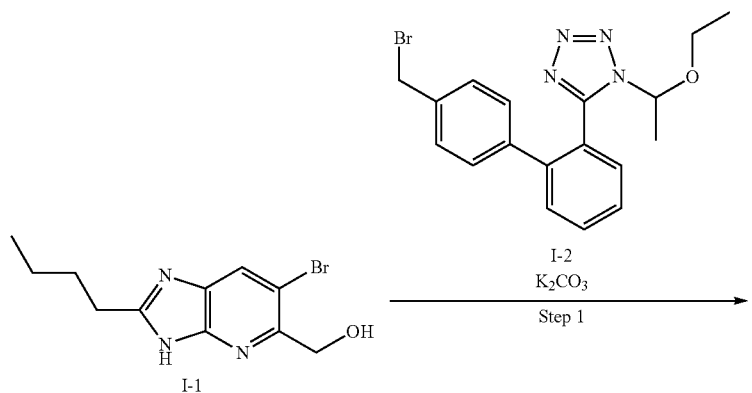

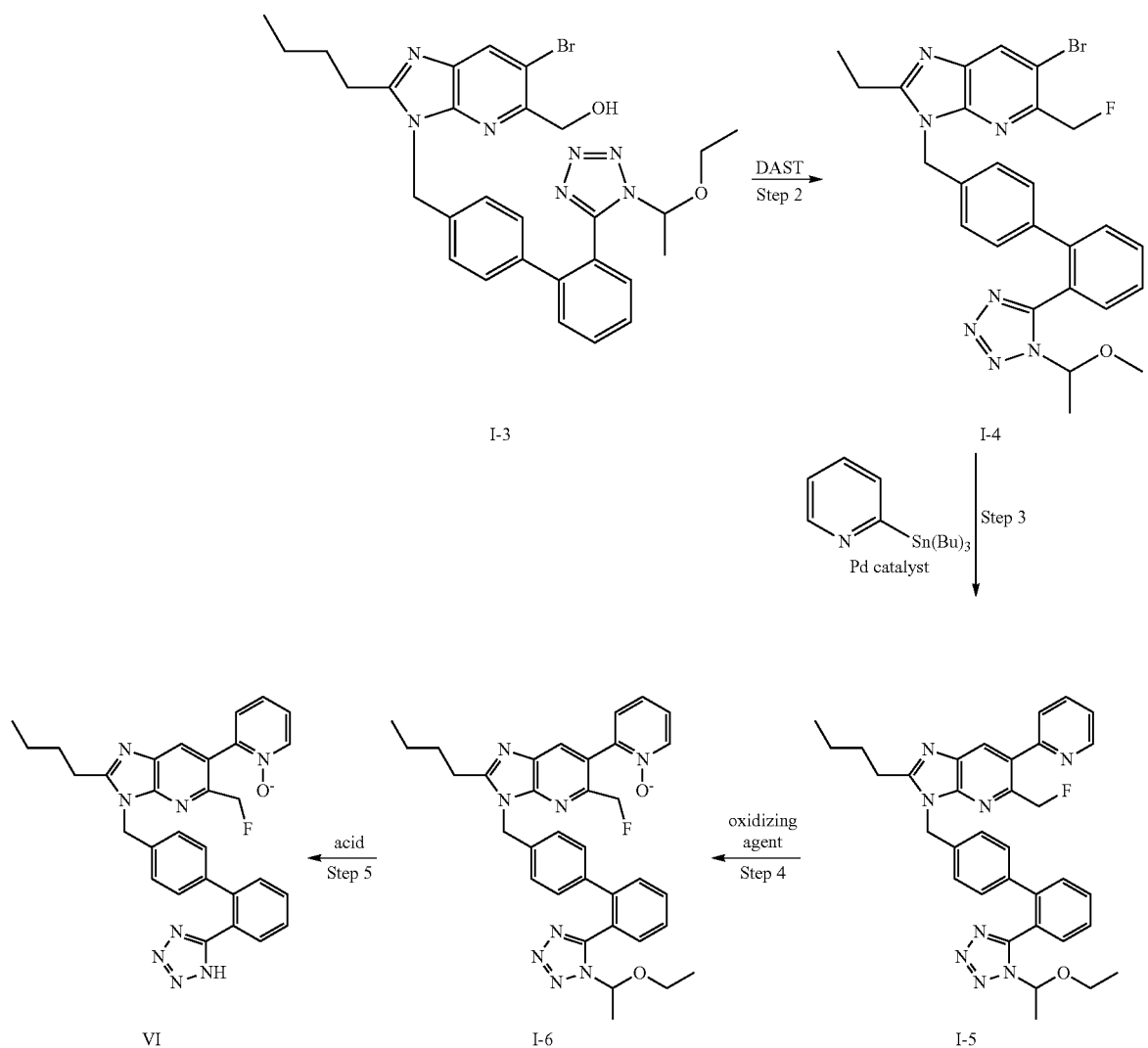

<Step 1>

The compound of formula (I-1) is subjected to an alkylation reaction with the compound of formula (I-2) in a solvent under a base condition to obtain the compound of formula (I-3). Preferably, the base is sodium hydroxide, sodium carbonate, potassium carbonate, or triethylamine, and the solvent is dimethylformamide (DMF), acetonitrile, or tetrahydrofuran (THF). The reaction may be conducted for 3 hours at room temperature.

<Step 2>

The compound of formula (I-3) is dissolved in dichloromethane and DAST (diethylaminosulfur trifluoride, 1.2 eq) is added dropwise thereto at −78° C. The resulting solution is then slowly warmed to 0° C. and allowed to react for 10 minutes to obtain the compound of formula (I-4).

<Step 3>

The compound of formula (I-4) is dissolved in toluene, and 2-tributyltin pyridine (1-3 eq) and tetrakis(triphenylphosiphine) palladium (0.03 eq) are added thereto. The resulting solution is kept at 120° C. for 15 hours to obtain the compound of formula (I-5).

<Step 4>

The compound of formula (I-5) is dissolved in a solvent, an oxidizing agent (1.3-5 eq) is added thereto, and the resulting solution is kept at room temperature for 1 to 10 hours to obtain the compound of formula (I-6). Preferably, the oxidizing agent is m-chloroperoxybenzoic acid (MCPBA), oxone, hydroperoxide, or peracetic acid, and the solvent is dichloromethane, acetone, methanol, acetic acid, or water. The reaction is preferably conducted in solvents of MCPBA (1.5 eq) and dichloromethane at room temperature for 5 hours.

<Step 5>

The compound of formula (I-6) is dissolved in methanol, ethanol, or tetrahydrofuran, an acid (1-5 eq) is added thereto, and the resulting solution is kept at room temperature for 10 minutes to 3 hours to obtain the compound of formula (VI) whose tetrazolyl group is unprotected. Preferably, the acid is anhydrous hydrochloric acid, hydrochloride, p-toluenesulfonic acid, MeSO$_3$H, or acetic acid.

The compounds of formulas (I-1) and (I-2) may be prepared according to the methods disclosed in WO 95/21838, WO 95/34564, and KR Patent Laid-open publications Nos. 96-00884 and 95-25039.

The compounds of formulas (VII) and (VIII) may be prepared according to Reaction scheme 2:

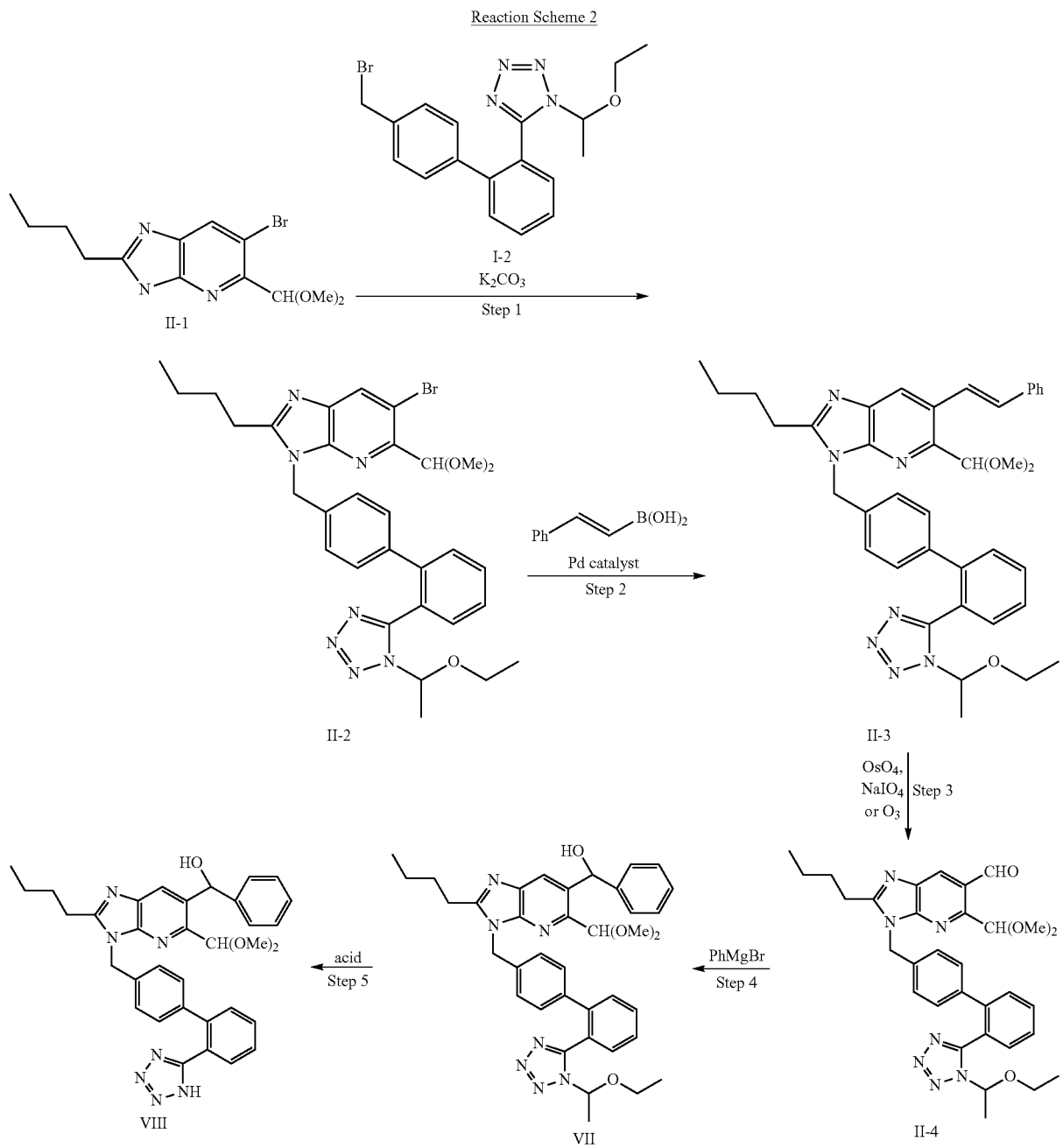

<Step 1>
The procedure of Step 1 of Reaction Scheme 1 is repeated except for using the compound of formula (II-1) as a starting material to obtain the compound of formula (II-2).

<Step 2>
The compound of formula (II-2) is dissolved in N,N-dimethylformamide, 1-phenylvinylboronic acid (1-1.5 eq) is added thereto, and then Pd(PPh$_3$)$_4$ (5 mol %), 3M Na$_2$CO$_3$ (2 eq) or Pd(OAc)$_2$ (3 mol %), PPh$_3$ (10 mol %) and triethylamine (2 eq) are added thereto. The resulting mixture is kept at 110° C. for 5 hours to obtain the compound of formula (II-3).

<Step 3>
The compound of formula (II-3) is dissolved in 1,4-dioxane/water (3:1), and then OsO$_4$ (3-10 mol %) and NaIO$_4$ (2-3 eq) are added thereto. The resulting mixture is kept at room temperature for 3 hours to obtain the compound of formula (II-4). Otherwise, the resulting mixture is dissolved in dichloromethane and then kept at −78° C. for 2 hours with adding ozone gas to obtain the compound of formula (II-4).

<Step 4>
The compound of formula (II-4) is dissolved in tetrahydrofuran or diethyl ether, and then PhMgBr or PhMgCl (1-2 eq)

is added thereto. The resulting mixture is kept at a temperature range of −78° C. to 0° C. for an hour to obtain the compound of formula (VII).

<Step 5>

The procedure of Step 5 of Reaction Scheme 1 is repeated except for using the compound of formula (VII) as a starting material to obtain the compound of formula (VIII).

The compounds of formulas (II-1) may be prepared according to the methods disclosed in WO 95/21838 and KR Patent Laid-open publications No. 95-25039.

The compounds of formulas (IX) and (X) may be prepared according to Reaction scheme 3:

Reaction Scheme 3

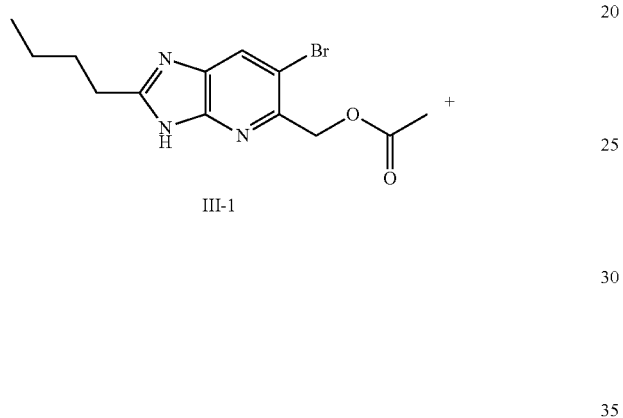

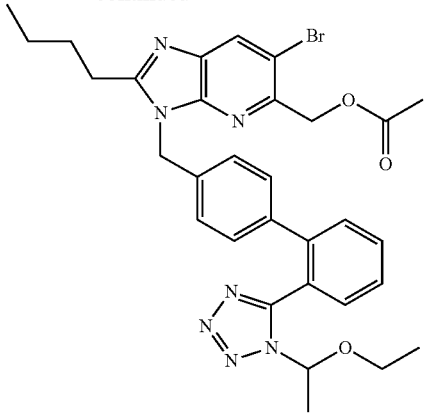

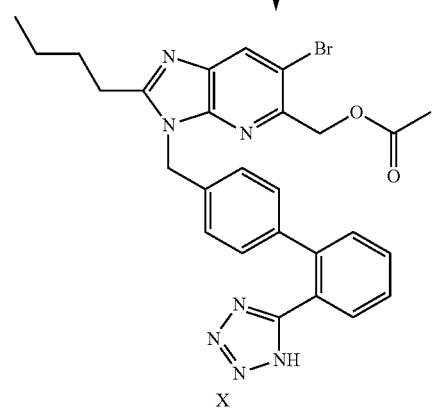

<Step 1>

The procedure of Step 1 of Reaction Scheme 1 is repeated except for using the compound of formula (III-1) as a starting material to obtain the compound of formula (IX).

<Step 2>

The procedure of Step 5 of Reaction Scheme 1 is repeated except for using the compound of formula (IX) as a starting material to obtain the compound of formula (X).

The compounds of formulas (III-1) may be prepared according to the methods disclosed in WO 95/21838, U.S. Pat. No. 5,691,348, and KR Patent Laid-open publications No. 95-25039.

The compound of formula (XI) may be prepared according to Reaction scheme 4:

Reaction Scheme 4

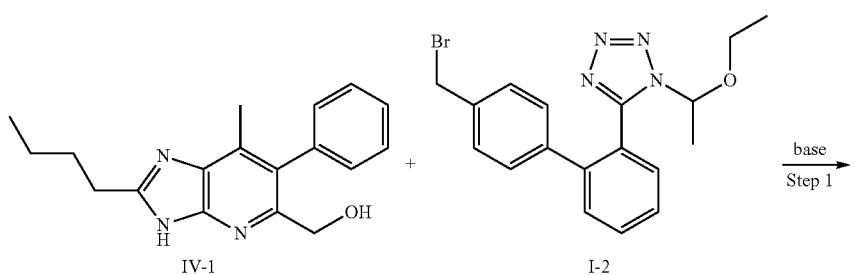

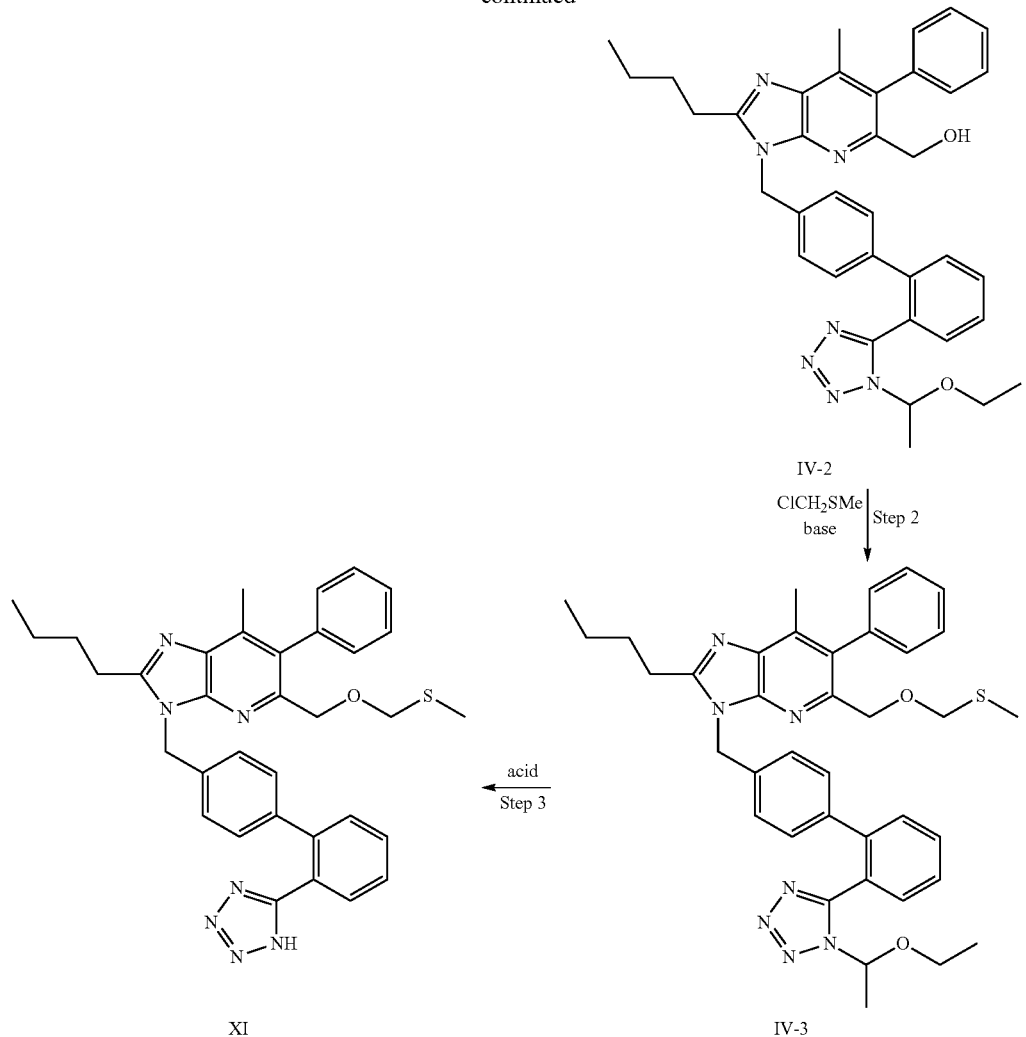

<Step 1>
The procedure of Step 1 of Reaction Scheme 1 is repeated except for using the compound of formula (IV-1) as a starting material to obtain the compound of formula (IV-2).
<Step 2>
The compound of formula (IV-2) is dissolved in N,N-dimethylformamide, and NaH (1.5 eq) is added thereto as a base, and then ClCH$_2$SMe (1.1 eq) and sodium iodide (0.3-1 eq) are added thereto. The resulting mixture is kept at a temperature range of 0° C. to room temperature for 3 hours to obtain the compound of formula (IV-3).

<Step 3>
The procedure of Step 5 of Reaction Scheme 1 is repeated except for using the compound of formula (IV-3) as a starting material to obtain the compound of formula (XI).

The compounds of formulas (IV-1) may be prepared according to the methods disclosed in WO 95/21838, U.S. Pat. No. 5,691,348, and KR Patent Laid-open publications No. 95-25039.

The compounds of formulas (XII) and (XIII) may be prepared according to Reaction scheme 5:

Reaction Scheme 5

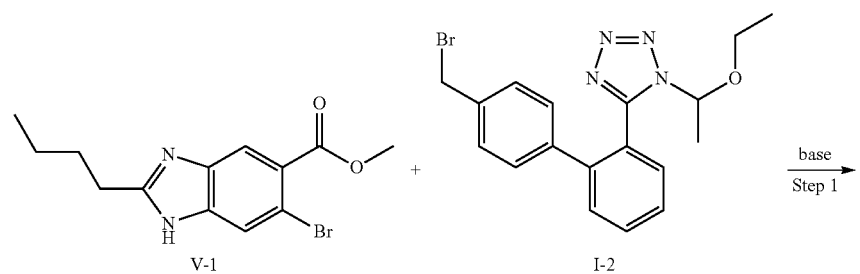

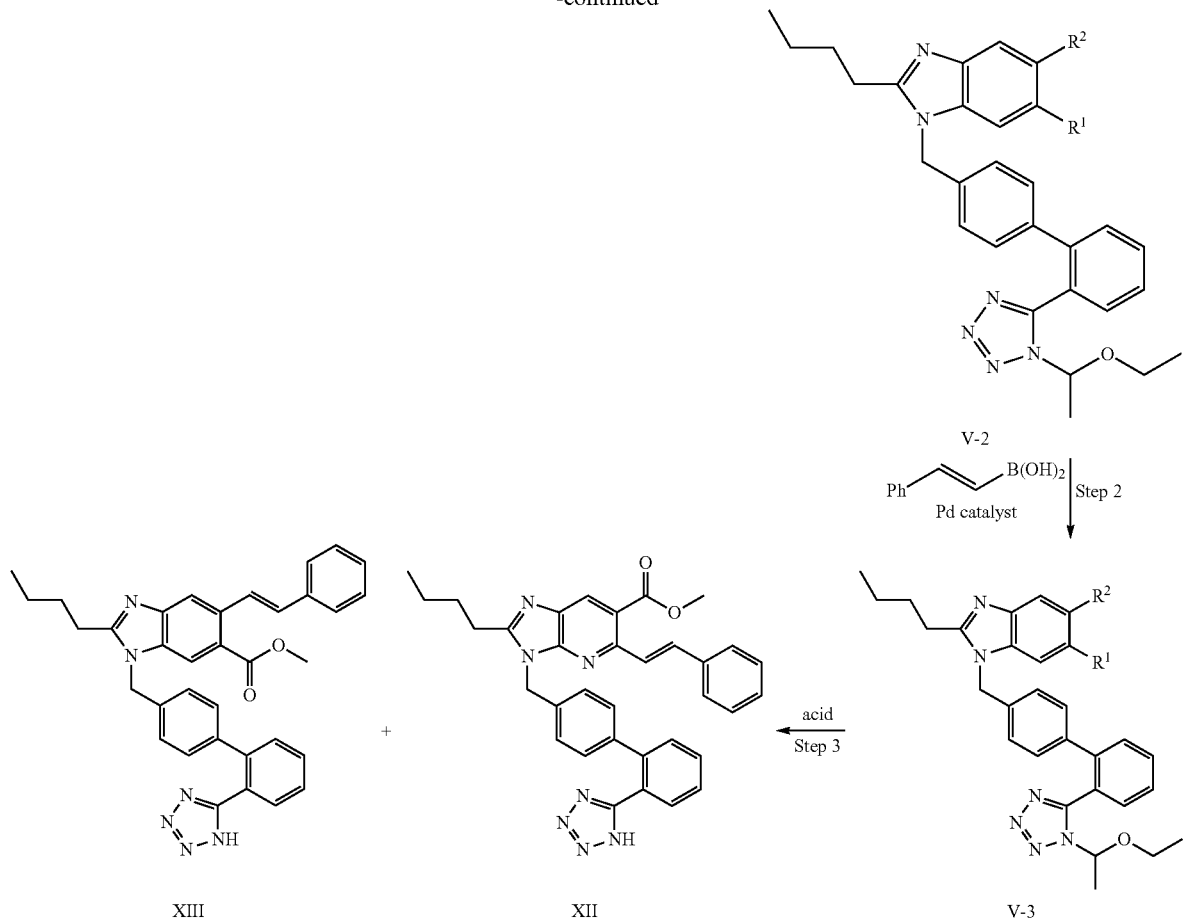

wherein, $R^1$ and $R^2$ are each independently Br or COOMe (in proviso that $R^1$ and $R^2$ are not same), and where $R^1$ in formula (V-2) is Br, $R^1$ in formula (V-3) is styryl, and where $R^1$ in formula (V-2) is COOMe, $R^2$ in formula (V-3) is styryl.

<Step 1>

The procedure of Step 1 of Reaction Scheme 1 is repeated except for using the compound of formula (V-1) as a starting material to obtain the compound of formula (V-2). The isomer may be obtained in the same amount.

<Step 2>

The procedure of Step 2 of Reaction Scheme 2 is repeated except for using the compound of formula (V-2) as a starting material to obtain the Suzuki coupled compound of formula (V-3).

<Step 3>

The procedure of Step 5 of Reaction Scheme 1 is repeated except for using the compound of formula (V-3) as a starting material to obtain the compounds of formulas (XII) and (XIII).

The compounds of formulas (V-1) may be prepared according to the methods disclosed in WO 95/21838, U.S. Pat. No. 5,691,348, and KR Patent Laid-open publication No. 95-25039.

The compound of formula (I) may be used in the form of a pharmaceutically acceptable addition salt formed with a free acid such as an organic or inorganic acid. Examples of such inorganic acid include hydrochloric acid, bromic acid, sulfuric acid, sulfurous, and phosphoric acids, preferably hydrochloric acid, while the organic acid may be citric acid, acetic acid, maleic acid, fumaric acid, gluconic acid, methanesulfonic acid, glycolic acid, succinic acid, tartaric acid, 4-toluenesulfonic acid, galacturonic acid, embonic acid, glutamic acid, and aspartic acids, preferably methanesulfonic acid.

The addition salt according to the present invention may be prepared by a conventional method, e.g., by dissolving the compound of formula (I) in a water-miscible organic solvent (e.g., acetone, methanol, ethanol, and acetonitrile) and adding thereto an organic or inorganic acid specified above in an equivalent or excessive amount, followed by the precipitation or crystallization, or evaporating a solvent or an excess acid, followed by the drying or the filtration of precipitated salts at a reduced pressure.

It should be understood to those skilled in the art that the present invention comprises not only the compound of formula (I) and a pharmaceutically acceptable salt thereof, but also a solvate, a hydrate, and a stereoisomer capable of being prepared therefrom within the scope of the present invention.

The compound of formula (I) of the present invention is characterized by the use for the prevention or treatment of osteoporosis, obesity, diabetes, or hyperlipidemia. The compounds of the present invention facilitate the translocation of transcription factor co-activator, protein TAZ into the nucleus (see Test 1), and the TAZ protein translocated not only inhibit the activity of PPARγ by binding each other to inhibit adipocyte differentiation (see Test 2), but also facilitate the RUNX2 activity by binding each other to facilitate osteoblast differentiation (see Test 3). Further, in experiments in vitro, the compounds of the present invention show the inhibition of adipocyte differentiation and the facilitation of osteoblast differentiation (see Test 4). Thus, the compound of formula (I) of the present invention can be used in the prevention or treatment of osteoporosis, obesity, diabetes, or hyperlipidemia.

The pharmaceutical compositions of the invention may be formulated for administration orally or parenterally.

The composition for oral administration may take various forms such as tablets, pill, soft and hard gelatin capsules, aqueous solutions, suspensions, emulsions, syrups, granules and elixirs, which may contain conventional additives such as a diluent (e.g., lactose, dextrose, sucrose, mannitol, sorbitol, cellulose and glycine), a lubricant (e.g., silica, talc, stearic acid or its magnesium or calcium salt, and polyethylene glycol). The tablet may also contain a binder (e.g., magnesium aluminum silicate, starch paste, gelatin, tragacanth, methyl cellulose, sodium carboxymethyl cellulose, and polyvinyl pyrrolidone) and optionally a disintegrant (e.g., starch, agar, and alginic acid or its sodium salt), absorbent, colorant, flavor, sweetener and the like.

The pharmaceutical compositions of the invention may be formulated for administration orally or parenterally, including subcutaneous, intravenous, intraperitoneal or intrathoracic injection. The parenteral formulation may be prepared in the unit dosage form by mixing the compound of formula (I) or a pharmaceutically acceptable salt with a stabilizer or buffer in water to obtain a solution or suspension, and packaging into amples or vials.

The composition may be sterilized and/or contain an adjuvant such as a preservative, stabilizer, wetting agent, emulsifier, a salt for controlling an osmotic pressure and/or a buffer solution, and other pharmaceutically effective materials, and may be formulated by any of conventional methods such as mixing, granulation, or coating.

The following Examples illustrate the present invention in more detail. However, these are merely examples, and the present invention is not limited thereto.

The molecular structures of the present invention were confirmed by infrared spectrometry, NMR spectroscopy, mass spectroscopy, liquid chromatography, X-ray crystallography, or comparison of ultimate analysis values for a representative compound with a real measurement values.

Example 1

Preparation of 2-butyl-5-fluoromethyl-6-(1-oxypyridin-2-yl)-3-[2'-(1H-tetrazol-5-yl)biphenyl-4-ylmethyl]-3H-imidazo[4,5-]pyridine (formula VI)

<1-1> Preparation of (2-butyl-3-{2'-[1-(1-ethoxyethyl)-1H-tetrazol-5-yl]biphenyl-4-ylmethyl}-6-bromo-3H-imidazo[4,5-b]pyridine-5-yl)methyanol (formula I-3)

(2-butyl-6-bromo-3H-imidazo[4,5-b]pyridine-5-yl)methanol (0.70 g, 2.49 mmol) was dissolved in 10 mL of N,N-dimethylformamide, and then potassium carbonate (1.03 g, 7.5 mmol) and 5-(4'-(bromomethyl)biphenyl-2-yl)-1-(1-ethoxyethyl)-1H-tetrazole (1.2 g, 3.0 mmol) were added to the resulting solution, followed by stirring the mixture at room temperature for 5 hours. 60 mL of water was added to the reaction mixture to dilute and extracted with ethyl acetate (60 mL×2). The organic layer was dried over anhydrous sodium sulfate and filtered, and then the solvent was removed. The resulting residue was concentrated under reduced pressure and refined by silica gel column chromatography (n-hexane:ethyl acetate=2:1) to obtain the title compound (0.92 g, yield: 63%.)

$^1$H-NMR(300 MHz, CDCl$_3$) δ 0.94(t, 3H), 1.06(t, 3H), 1.43(m, 2H), 1.64(d, 3H), 1.82(m, 2H), 2.84(t, 2H), 3.23(m, 1H), 3.42(m, 1H), 4.18(t, 1H, OH), 4.71(d, 2H), 5.52(s, 2H), 5.87(q, 1H), 7.09-7.17(m, 4H), 7.32-7.53(m, 3H), 7.86(d, 1H), 7.89(s, 1H); MS(m/e, M$^+$): 590.

<1-2> Preparation of methanesulfonic acid 2-butyl-3-{2'-[1-(1-ethoxyethyl)-1H-tetrazol-5-yl]biphenyl-4-ylmethyl}-6-bromo-5-fluoromethyl-3H-imidazo[4,5-b]pyridine (formula I-4)

The compound of formula (I-3) (0.56 g, 0.95 mmol) obtained in step <1-1> was dissolved in 10 mL of dichloromethane, and then cooled to -78° C. and diethylaminosulfur trifluoride (DAST, 0.14 mL, 1.05 mmol) was slowly added dropwise thereto. The resulting solution was warmed to 0° C., stirred for about another 10 minutes and water was added thereto to finish the reaction. The reaction mixture was diluted with 50 mL of water and extracted with ethyl acetate (50 mL×2). The organic layer was dried over anhydrous sodium sulfate and filtered, and then the solvent was removed. The resulting residue was concentrated under reduced pressure and refined by silica gel column chromatography (n-hexane:ethyl acetate=2:1) to obtain the title compound (0.32 g, yield: 57%.)

$^1$H-NMR(300 MHz, CDCl$_3$) δ 0.90(t,3H), 1.06(t,3H), 1.39 (m,2H), 1.63(d,3H), 1.76(m,2H), 2.80(t,2H), 3.20(m,1H), 3.42(m,1H), 5.46(s,2H), 5.59 and 5.75(s,1H, CH2F), 5.87(q, 1H), 7.05(d,2H), 7.13(d,2H), 7.37-7.53(m,3H), 7.86(dd,1H), 8.18(s,1H); MS(m/e, M$^+$): 592.

<1-3> Preparation of 2-butyl-3-{2'-[1-(1-ethoxyethyl)-1H-tetrazol-5-yl]biphenyl-4-ylmethyl}-5-fluoromethyl-6-pyridine-2-yl-3H-imidazo[4,5-b]pyridine (formula I-5)

The compound of formula (I-4) (200 mg, 0.34 mmol) obtained in step <1-2> was dissolved in 10 mL of toluene, and then 2-tributyltin pyridine (250 mg, 0.68 mmol) and Pd(PPh$_3$)$_4$ (20 mg, 0.017 mmol) were added thereto, followed by reacting at 120° C. for 16 hours. The solvent was removed and the resulting residue was concentrated under reduced pressure and then refined by silica gel column chromatography (1. n-hexane:ethyl acetate (1:1); 2. ethyl acetate) to obtain the title compound as an oil (160 mg, yield: 80%).

$^1$H-NMR(300 MHz, CDCl$_3$) δ 0.92(t, 3H), 1.07(t,3H), 1.41(m,2H), 1.64(d,3H), 1.81(m,2H), 2.83(t,2H), 3.20(m, 1H), 3.42(m,1H), 5.54(dd, 2H), 5.58 and 5.74(s,1H, CH2F), 5.87(q,1H), 7.12(d,2H), 7.15(d,2H), 7.41-7.61(m, 5H), 7.84 (m, 2H), 8.13(s,1H), 8.72(d, 1H); MS(m/e, M$^+$): 590.

<1-4> Preparation of 2-butyl-3- {2'-[1-(1-ethoxyethyl)-1H-tetrazol-5-yl]biphenyl-4-ylmethyl}-5-fluoromethyl-6-(1-oxypyridin-2-yl)-3H-imidazo[4,5-b]pyridine (formula I-5)

The compound of formula (I-5) (240 mg, 0.40 mmol) obtained in step <1-3> was dissolved in 5 mL of dichloromethane, and then m-chloroperoxybenzoic acid (m-CPBA, 200 mg, 0.81 mmol) was added thereto, followed by stirring at room temperature for 3 hours. The solvent was removed and the resulting residue was concentrated under reduced pressure and then refined by silica gel column chromatography (1. n-hexane:ethyl acetate (1:1); 2. 5% methanol/dichloromethane) to obtain the title compound as a solid (170 mg, yield: 70%).

$^1$H-NMR(300 MHz, CDCl$_3$) d 0.92(t, 3H), 1.08(t,3H), 1.42(m,2H), 1.65(d,3H), 1.80(m,2H), 2.83(t,2H), 3.20(m, 1H), 3.42(m,1H), 5.52(s, 2H), 5.46 and 5.62(s,1H, CH$_2$F), 5.87(q,1H), 7.13-7.14(m,4H), 7.37-7.53(m, 6H), 7.86(dd, 1H), 8.00(s,1H), 8.45(d, 1H); MS(m/e, M$^+$): 606.

<1-5> Preparation of 2-butyl-5-fluoromethyl-6-(1-oxypyridin-2-yl)-3-[2-(1H-tetrazl-5-yl)biphenyl-4-ylmethyl]-3H-imidazo[4,5-b]pyridine (formula VI)

The compound of formula I-6 (120 mg, 0.19 mmol) obtained in step <1-4> was dissolved in 3 mL of methanol, and then 1 mL of 3N-HCl was added thereto, followed by stirring at room temperature for 20 minutes. The reaction mixture is adjust to about pH 4 by adding 1N-NaOH, diluted in 20 mL of water and extracted with ethyl acetate (20 mL×2), and then the organic layer was dried over anhydrous sodium sulfate and filtered. The solvent was removed, and the resulting residue was concentrated under reduced pressure and then refined by n-hexane/ethyl acetate to obtain the title compound (100 mg, yield: 94%).

$^1$H-NMR(300 MHz, CDCl$_3$) δ 0.78(t, 3H), 1.29(m, 2H), 1.60(br-s, 2H), 2.66(br-s, 2H), 5.10 and 5.45(d, 2H), 5.60(br-s, 2H), 6.73(d, 2H), 6.95(d, 2H), 7.15(d, 1H), 7.39-7.48(m, 5H), 7.48(d, 1H), 7.75(s, 1H), 8.38(d, 1H); FAB-MS (m/e, M$^+$): 535(M$^+$+1).

Example 2

Preparation of (2-butyl-5-dimethoxymethyl-3-{2'-[1-(1-ethoxyethyl)-1H-tetrazol-5-yl]biphenyl-4-ylmethyl}-3H-imidazo[4,5-b]pyridin-6-yl)phenylmethanol (formula VII)

<2-1> Preparation of 6-bromo-2-butyl-5-dimethoxymethyl-3-{2'-[1-(1-ethoxyethyl)-1H-tetrazol-5-yl]biphenyl-4-ylmethyl}-3H-imidazo[4,5-b]pyridine (formula II-2)

The procedure of <1-1> was repeated except for using 6-bromo-2-butyl-5-dimethoxymethyl-3H-imidazo[4,5-b]pyridine (1.8 g, 5.48 mmol) instead of a compound of formula (I-1) to obtain the title compound (1.91 g, yield: 55%).

$^1$H-NMR(300 MHz, CDCl$_3$) δ 0.92(t, 3H), 1.06(t, 3H), 1.42(m, 2H), 1.63(d, 3H), 1.79(m, 2H), 2.79(t, 2H), 3.21(m, 1H), 3.42(m, 1H), 3.48(s, 6H), 5.47(s, 2H), 5.79(s, 1H), 5.86 (q, 1H), 7.08(d, 2H), 7.12(d, 2H), 7.37(dd, 1H), 7.44-7.55(m, 2H), 7.85(dd, 1H), 8.16(s, 1H); MS(m/e, M$^+$): 634.

<2-2> Preparation of 2-butyl-5-dimethoxymethyl-3-{2'-[1-(1-ethoxyethyl)-1H-tetrazol-5-yl]biphenyl-4-ylmethyl}-6-styryl-3H-imidazo[4,5-b]pyridine (formula II-3)

The compound of formula (II-2) obtained in <2-1> (0.5 g, 0.79 mmol) was suspended in 10 mL of 1,2-dimethoxyethane, and 350 mg of trans-2-phenylvinylboronic acid (2.37 mmol, 3 eq), 46 mg of Pd(PPh$_3$)$_4$ (0.04 mmol, 0.05 eq) and 0.79 mL of 3M-Na$_2$CO$_3$ (2.37 mmol, 3 eq) were added thereto, followed by stirring with reflux at 90° C. for 5 hours. The resulting mixture was diluted with 60 mL of ethyl acetate, filtered through celite, and concentrated by evaporation under a reduced pressure. The resulting residue was purified by silica gel column chromatography (n-hexane: ethyl acetate=2:1) to obtain the title compound as a yellowish solid (355 mg, yield: 68%).

$^1$H-NMR(300 MHz, CDCl$_3$): δ 0.93(t, 3H), 1.08(t, 3H), 1.43(m, 2H), 1.66(d, 3H), 1.81(m, 2H), 2.80(t, 2H), 2.80(t, 2H), 3.23(m, 1H), 3.46(m, 1H), 3.48(s, 6H), 5.49(d, 2H), 5.55(s, 1H), 5.87(q, 1H), 7.00(d, 1H, J=16.2 Hz), 7.11(m, 3H), 7.29(m, 2H), 7.39(m, 3H), 7.51(m, 2H), 7.55(m, 2H), 7.88(m, 2H), 8.29(s, 1H); MS(m/e, M$^+$): 657.

<2-3> Preparation of 2-butyl-5-dimethoxymethyl-3-{2'-[1-(1-ethoxyethyl)-1H-tetrazol-5-yl]biphenyl-4-ylmethyl}-3H-imidazo[4,5-b]pyridine-6-carbaldehyde (formula II-4)

The compound of formula (II-3) obtained in <2-2> (355 mg, 0.54 mmol) was suspended in 6 mL of 1,4-dioxane and 2 mL of water, and 346 mg of NaIO$_4$ (1.62 mmol, 3 eq.) and OsO$_4$ (2.5 wt % in 2-methyl-2-propanol) as catalysts were added thereto, followed by stirring at room temperature for 2 hours. Then, the resulting mixture was diluted with 15 mL of water and washed with water and a brine while extracting with ethyl acetate (15 mL). The extracted organic layer was dried over anhydrous sodium sulfate, filtered, and concentrated by evaporation under a reduced pressure. The resulting residue was purified by silica gel column chromatography (n-hexane:ethyl acetate=1:1) to obtain the title compound as a yellowish oil (255 mg, yield: 81%).

$^1$H-NMR(300 MHz, CDCl$_3$): δ 0.92(t, 3H), 1.07(t, 3H), 1.41(m, 2H). 1.65(d, 3H), 1.80(m, 2H), 2.81(t, 2H), 3.23(m, 1H), 3.45(m, 1H), 3.51(s, 6H), 5.51(s, 1H), 5.89(q, 1H), 7.08(d, 2H, J=8.1 Hz), 7.14(d, 2H, J=8.3 Hz), 7.40(dd 1H, J=1.7, 7.5 Hz), 7.51(m, 2H), 7.87(dd, 1H, J=1.7, 7.5 Hz), 8.61(s, 1H), 10.75(s, 1H, —CHO); MS(m/e, M$^+$): 583.

<2-4> Preparation of (2-butyl-5-dimethoxymethyl-3-{2'-[1-(1-ethoxyethyl)-1H-tetrazol-5-yl]biphenyl-4-ylmethyl}-3H-imidazo[4,5-b]pyridine-6-yl)phenyl-methanol (formula VII)

The compound of formula (II-4) obtained in <2-3> (255 mg, 0.44 mmol) was suspended in 6 mL of tetrahydrofuran, and 0.44 mL of phenyl magnesium bromide solution (3.0M solution dissolved in diethyl ether) (1.31 mmol, 3 eq.) was added thereto at −78° C., followed by stirring at same temperature for 30 min. Then, the resulting mixture was diluted with 15 mL of water and washed with water and a brine while extracting with ethyl acetate (15 mL). The extracted organic layer was dried over anhydrous sodium sulfate, filtered, and concentrated by evaporation under a reduced pressure. The resulting residue was purified by silica gel column chromatography (n-hexane:ethyl acetate=1:2) to obtain the title compound as whitish foam (220 mg, yield: 76%).

$^1$H-NMR(300 MHz, CDCl$_3$): δ 0.90(t, 3H), 1.07(t, 3H), 1.38(m, 2H). 1.65(d, 3H), 1.77(m, 2H), 2.74(t, 2H), 3.22(m, 1H), 3.43(m, 1H), 3.49(s, 3H), 3.59(s, 3H), 3.67(s, 1H), 5.47 (s, 2H), 5.52(s, 1H), 5.88(q, 1H), 6.77(s, 1H), 7.11(m, 4H), 7.39(m, 3H), 7.50(m 4H), 7.70(s, 1H), 7.87(d, 1H, J=7.2 Hz); MS(m/e, M$^+$): 661.

Example 3

Preparation of {2-butyl-5-dimethoxymethyl-3-[2'-(1H-tetrazol-5-yl)biphenyl-4-ylmethyl]-3H-imidazo [4,5-b]pyridin-6-yl}phenylmethanol (formula VIII)

The procedure of <1-5> was repeated except for using the compound of formula (VII) (100 mg, 0.15 mmol) instead of a compound of formula (I-6) to obtain the title compound (80 mg, yield: 90%).

¹H-NMR(300 MHz, CDCl₃): δ 0.85(t, 3H), 1.31(m, 2H), 1.65(m, 2H), 2.63(t, 2H), 3.41(s, 3H), 3.50(s, 3H), 5.38(m, 2H), 5.54(s, 1H), 6.64(s, 1H), 6.97(m, 4H), 7.36(m, 3H), 7.41(d, 2H, J=7.1 Hz), 7.53(m, 2H), 7.65(s, 1H), 7.93(d, 1H, J=7.5 Hz); MS(m/e, M⁺): 589.

Example 4

Preparation of 6-bromo-2-butyl-3-{2'-[1-(1-ethoxyethyl)-1H-tetrazol-5-yl]biphenyl-4-ylmethyl}-3H-imidazo[4,5-b]pyridin-5-ylmethyl acetate (formula IX)

The procedure of <1-1> was repeated except for using 6-bromo-2-butyl-3H-imidazo[4,5-b]pyridine-5-ylmethyl acetate of formula (III-1) (300 mg, 0.92 mmol) instead of a compound of formula (I-1) to obtain the title compound (340 mg, yield: 59%).

¹H-NMR(300 MHz, CDCl₃): δ 8.16(s, 1H), 7.88(dd, J=7.5, 1.6 Hz, 1H), 7.50(m, 2H), 7.41(dd, J=7.5, 1.6 Hz, 1H), 7.14(d, J=8.4 Hz, 2H), 7.08(d, J=8.4 Hz, 2H), 5.88(q, 1H), 5.42(m, 4H), 3.42(m, 1H), 3.20(m, 1H), 2.80(t, 2H), 2.14(s, 3H), 1.78(m 2H), 1.63(d, J=6.0 Hz, 3H), 1.41(m, 2H), 1.05(t, 3H), 0.92(t, 3H).

Example 5

Preparation of 6-bromo-2-butyl-3-[2'-(1H-tetrazol-5-yl)biphenyl-4-ylmethyl]-3H-imidazo[4,5-b]pyridin-5-ylmethyl acetate (formula X)

The procedure of <1-5> was repeated except for using the compound of formula (IX) obtained in Example 4 (150 mg, 0.23 mmol) instead of a compound of formula (I-6) to obtain the title compound (126 mg, yield: 95%).

¹H-NMR(300 MHz, CDCl₃) δ 7.98(d, J=7.3 Hz, 1H), 7.58-7.67(m, 3H), 7.42(d, J=7.3 Hz, 1H), 7.03(d, J=6.8 Hz, 2H), 6.94(d, J=6.8 Hz, 2H), 5.41(s, 2H), 5.36(s, 2H), 2.73(t, 2H), 2.10(s, 3H), 1.69(m, 2H), 1.35(m, 2H), 0.89(t, 2H).

Example 6

Preparation of 2-butyl-7-methyl-5-[(methylsulfanylmethoxy)methyl]-6-phenyl-3-[2'-(1H-tetrazol-5-yl)biphenyl-4-ylmethyl]-3H-imidazo[4,5-b]pyridine (formula XI)

<6-1> Preparation of (2-butyl-3-{2'-[1-(1-ethoxyethyl)-1H-tetrazol-5-yl]biphenyl-4-ylmethyl}-7-methyl-6-phenyl-3H-imidazo[4,5-b]pyridine-5-yl)-methanol (formula IV-2)

The procedure of <1-1> was repeated except for using (2-butyl-7-methyl-6-phenyl-3H-imidazo[4,5-b]pyridine-5-yl)methanol of formula (IV-1) (0.5 g, 1.69 mmol) instead of a compound of formula (I-1) to obtain the title compound (0.58 g, yield: 57%).

¹H-NMR(300 MHz, CDCl₃): δ 0.92(t, 3H), 1.08(t 3H), 1.40(m, 2H), 1.66(d, 3H), 1.78(m, 2H), 2.35(s, 3H), 2.75(t, 2H), 3.24(m, 1H), 3.42(m, 1H), 4.78(d, 2H, J=5.3 Hz), 5.28(t, 1H, —OH), 5.48(s, 2H), 5.87(q, 1H), 7.15(m, 4H), 7.21(d, 2H, J=7.8 Hz), 7.39-7.54(m, 6H) 7.88(dd, 1H, J=1.0, 7.3 Hz); Mass: 601.

<6-2> Preparation of 2-butyl-3-{2'-[1-(1-ethoxyethyl)-1H-tetrazol-5-yl]biphenyl-4-ylmethyl}-7-methyl-5-methylsulfanylmethoxymethyl-6-phenyl-3H-imidazo[4,5-b]pyridine (formula IV-3)

The compound of formula (IV-2) obtained in <6-1> (0.53 g, 0.88 mmol) was suspended in 5 mL of N,N-dimethylformamide, cooled to 0° C., and sodium hydride (60%; 53 mg, 1.32 mmol), chloromethyl methylsulfide (0.12 mL, 1.32 mmol) and NaI (0.13 g, 0.88 mmol) were added thereto, followed by stirring at room temperature for 3 hours. Then, the resulting mixture was diluted with 50 mL of water and extracted with ethyl acetate (50 mL×2). The organic layer was dried over anhydrous sodium sulfate, filtered, and concentrated by evaporation under a reduced pressure. The resulting residue was purified by silica gel column chromatography (n-hexane:ethyl acetate=3:1) to obtain the title compound (0.49 g, yield: 85%).

¹H-NMR(300 MHz, CDCl₃): δ 0.93(t, 3H), 1.10(t 3H), 1.38(m, 2H), 1.70(d, 3H), 1.76(m, 2H), 2.07(s, 3H), 2.35(s, 3H), 2.76(t, 2H), 3.23(m, 1H), 3.45(m, 1H), 4.50(s, 2H), 4.95(s, 2H), 5.45(s, 2H), 5.84(q, 1H), 7.10(m, 4H), 7.20(d, 2H,), 7.25-7.50(m, 6H) 7.90(m, 1H); Mass: 661.

<6-3> Preparation of 2-butyl-7-methyl-5-[(methylsulfanylmethoxy)methyl]-6-phenyl-3-[2'-(1H-tetrazol-5-yl)biphenyl-4-ylmethyl]-3H-imidazo[4,5-b]pyridine (formula XI)

The procedure of <1-5> was repeated except for using the compound of formula (IV-3) obtained in Example <6-2> (0.22 g, 0.33 mmol) instead of a compound of formula (I-6) to obtain the title compound (0.18 g, yield: 91%).

¹H-NMR(300 MHz, CDCl₃): δ 0.95(t, 3H), 1.43(m, 2H), 1.80(m, 2H), 2.07(s, 3H), 2.35(s, 3H), 2.85(t, 2H), 4.55(s, 2H), 4.85(s, 2H), 5.30(s, 2H), 7.00(m, 4H), 7.20(m, 2H), 7.32(m, 2H) 7.45(m, 5H); Mass: 589.

Example 7

Preparation of methyl 2-butyl-6-styryl-1-[2'-(1H-tetrazol-5-yl)biphenyl-4-ylmethyl]-1H-benzimidazol-5-carboxylate (formula XII)

<7-1> Preparation of methyl 6-bromo-2-butyl-1-{2'-[1-(1-ethoxyethyl)-1H-tetrazol-5-yl]biphenyl-4-ylmethyl]-1H-benzimidazol-5-carboxylate (formula V-2a; R¹=Br, R²=COOMe) and methyl 5-bromo-2-butyl-1-{2'-[1-(1-ethoxyethyl)-1H-tetrazol-5-yl]biphenyl-4-ylmethyl]-1H-benzimidazol-6-carboxylate (formula V-2b; R¹=COOMe, R²=Br)

The procedure of <1-1>was repeated except for using methyl 6-bromo-2-butyl-1H-benzimidazol-5-carboxylate of formula (V-1) (2.5 g, 8.0 mmol) instead of a compound of formula (I-1) to obtain the title compounds of formula (V-2a) (1.87 g, yield: 38%) and formula (V-2b) (1.97 g, yield: 40%) as oils.

¹H-NMR(300 MHz, CDCl₃) V-2a: δ 0.93(t, 3H), 1.05(t, 3H), 1.42(m, 2H), 1.65(d, 3H), 1.82(m, 2H), 2.83(t, 2H), 3.22(m, 1H), 3.43(m, 1H), 3.93(s, 3H), 5.34(s, 2H), 5.86(q, 1H), 6.93(d, 1H, J=8.1 Hz), 7.16(d, 1H, J=8.1 Hz), 7.46(d, 1H, J=7.5 Hz), 7.46-7.57(m, 2H), 7.50(s, 1H), 7.89(d, 1H, J=7.5 Hz), 8.24(s, 1H); Mass: 619.

¹H-NMR(300 MHz, CDCl₃) V-2b: δ 0.93(t, 3H), 1.04(t, 3H), 1.43(m, 2H), 1.64(d, 3H), 1.81(m, 2H), 2.82(t, 2H), 3.21(m, 1H), 3.42(m, 1H), 3.91(s, 3H), 5.34(s, 2H), 5.86(q, 1H), 6.93(d, 1H, J=8.0 Hz), 7.14(d, 1H, J=8.0 Hz), 7.40(d, 1H, J=7.6 Hz), 7.46-7.56(m, 2H), 7.76(s, 1H), 7.88(d, 1H, J=7.6 Hz), 8.02(s, 1H); Mass: 619.

<7-2> Preparation of methyl 2-butyl-1-{2'-[1-(1-ethoxyethyl)-1H-tetrazol-5-yl]biphenyl-4-ylmethyl]-6-styryl-1H-benzimidazol-5-carboxylate (formula V-3a; R¹=styryl, R²=COOMe) and methyl 2-butyl-1-{2'-[1-(1-ethoxyethyl)-1H-tetrazol-5-yl]biphenyl-4-ylmethyl}-5-styryl-1H-benzimidazol-6-carboxylate (formula V-3b; R¹=COOMe, R²=styryl)

The procedure of <2-2> was repeated except for using the compound of formula (V-2) obtained in Example <7-2> (1.0 g, 1.62 mmol) instead of a compound of formula (II-2) to obtain the title compounds of formula (V-3a) (0.72 g, yield: 70%) and formula (V-3b) (0.69 g, yield: 67%) as oils.

¹H-NMR(300 MHz, CDCl₃) V-3a: δ 0.92(t, 3H), 1.01(t, 3H), 1.45(m, 2H), 1.61(d, 3H), 1.84(m, 2H), 2.84(t, 2H), 3.20(m, 1H), 3.36(m, 1H), 3.92(s, 3H), 5.39(s, 2H), 5.80(q, 1H), 6.85(d, 1H, J=16.2 Hz), 6.98(d, 1H, J=8.2 Hz), 7.16(d, 1H, J=8.2 Hz), 7.24(m, 1H), 7.31-7.36(m, 2H), 7.41(dd, 1H), 7.47-7.55(m, 4H), 7.48(s, 1H), 7.88(dd, 1H), 8.08(d, 1H, J=16.1 Hz), 8.38(s, 1H); Mass: 642.

¹H-NMR(300 MHz, CDCl₃) V-3b: δ 0.94(t, 3H), 1.06(t, 3H), 1.45(m, 2H), 1.64(d, 3H), 1.85(m, 2H), 2.83(t, 2H), 3.22(m, 1H), 3.42(m, 1H), 3.91(s, 3H), 5.36(s, 2H), 5.87(q, 1H), 6.95(d, 1H, J=8.2 Hz), 6.98(d, 1H, J=15.8 Hz), 7.27(m, 1H), 7.33-7.58(m, 7H), 7.87(d, 1H, J=7.6 Hz), 7.90(s, 1H), 8.05(s, 1H), 8.07(d, 1H, J=15.8 Hz); Mass: 642.

<7-3> Preparation of methyl 2-butyl-6-styryl-1-[2'-(1H-tetrazol-5-yl)biphenyl-4-ylmethyl]-1H-benzimidazol-5-carboxylate (formula XII)

The procedure of <1-5> was repeated except for using the compound of formula (V-3a) obtained in Example <7-2> (0.21 g, 0.32 mmol) instead of a compound of formula (I-6) to obtain the title compound (0.154 g, yield: 85%).

¹H-NMR(300 MHz, CDCl₃): δ0.83(t, 3H), 1.29(m, 2H), 1.59(m, 2H), 2.41(t, 2H), 3.89(s, 3H), 5.29(s, 2H), 6.71(d, 2H, J=8.1 Hz), 6.76(d, 1H, J=16.1 Hz), 6.91(d, 2H, J=8.1 Hz), 7.23-7.32(m, 5H), 7.37(s, 1H), 7.47(s, 1H), 7.49(m, 1H), 7.54-7.65(m, 2H), 7.90(d, 1H, J=16.1 Hz), 8.00(dd, 1H); Mass: 568.

Example 8

Preparation of methyl 2-butyl-5-styryl-1-[2'-(1H-tetrazol-5-yl)biphenyl-4-ylmethyl]-1H-benzimidazol-6-carboxylate (formula XIII)

The procedure of <1-5> was repeated except for using the compound of formula (V-3b) obtained in Example <7-2> (0.25 g, 0.39 mmol) instead of a compound of formula (I-6) to obtain the title compound (0.19 g, yield: 87%).

¹H-NMR(300 MHz, CDCl₃): δ 0.86(t, 3H), 1.30(m, 2H), 1.62(m, 2H), 2.44(t, 2H), 3.88(s, 3H), 5.26(s, 2H), 6.62(d, 1H, J=16.0 Hz), 6.71(d, 2H, J=8.1 Hz), 6.92(d, 2H, J=8.1 Hz), 7.14(s, 1H), 7.29-7.34(m, 2H), 7.37-7.43(m, 2H), 7.49-7.55 (m, 4H), 7.62(s, 1H), 7.85(d, 1H, J=16.0 Hz), 7.98(m, 1H); Mass: 568.

The substituents of the compounds of the present invention were summarized and shown in following Table 2.

TABLE 2

Substituents of the compounds of formula (I)

| Compound (formula No) | R¹ | R² | R³ | A | X | P |
|---|---|---|---|---|---|---|
| II | —CH₂OH | H | Me | ethyl | N | H |
| III | Me | pyridin-3-yl | H | n-butyl | N | H |
| IV | —CO₂Me | pyridin-2-yl | H | n-butyl | N | H |
| V | —CH₂OH | H | Me | n-butyl | N | H |
| VI | —CH₂F | pyridine N-oxide (2-yl) | H | n-butyl | N | H |
| VII | —CH(OMe)₂ | phenyl-CH(OH)- | H | n-butyl | N | 1-ethoxyethyl |
| VIII | —CH(OMe)₂ | phenyl-CH(OH)- | H | n-butyl | N | H |
| IX | —CH₂OAc | Br | H | n-butyl | N | 1-ethoxyethyl |

TABLE 2-continued

Substituents of the compounds of formula (I)

| Compound (formula No) | R¹ | R² | R³ | A | X | P |
|---|---|---|---|---|---|---|
| X | —CH₂OAc | Br | H | n-butyl | N | H |
| XI | —CH₂OCH₂SMe | phenyl | H | n-butyl | N | H |
| XII | (3-methyl-cinnamyl group) | COOMe | H | n-butyl | CH | H |
| XIII | —CO₂Me | (3-methyl-cinnamyl group) | H | n-butyl | CH | H |

The compounds of formulas (II) to (XIII) were evaluated for pharmaceutical efficacy according to the following procedures.

Test 1. Effect on Stimulating TAZ Protein Migration Toward Nucleus

Vector pEGFP-TAZ in which GFP (green fluorescence protein) is linked to protein TAZ was prepared, and nucleus specific histone protein (RFP-H2B) expression vector having introduced RFP (red fluorescence protein) therein was prepared. The vector pEGFP-TAZ was prepared by introducing full length TAZ cDNA synthesized by PCR method into vector pEGFP (Invitrogen, Carlsbad, Calif., USA) and then cloning. The expression vector RFP-H2B was prepared by introducing full length histone H2B cDNA into expression vector RFP (Clontech Laboratories, Inc., Palo Alto, Calif., USA) and then cloning.

Cos7 cells (ATCC, Manassas, Va.) were distributed to each well of a 96-well plate (5×10³ cells/well) and stabilized, and then vectors pEGFP-TAZ and RFP-H2B were introduced into the cells by employing Effectene™ (Qiagen). After 48 hours, the cells were treated with each of the inventive compounds to a concentration of 10 μM. After 30 minutes, the movement of green fluorescent color toward the cell nucleus was observed continually by employing BD Pathway™ high-content bio-imager (BD bioscience). Using a quantification program (BD IPLab™ for Pathway and BD™ Image Data Explorer), GFP expression in the nucleus of RFP-expressed cells was quantified.

GFP expressions of protein TAZ in the nucleus were analyzed and calculated in percentage term based on that of non-treated cells in a control group, which are shown in Table 3.

As shown in Table 3, the inventive compounds promoted the migration of protein TAZ toward nucleus by more than 130%. Accordingly, the inventive compounds are each expected to affect the differentiation into adipocytes or osteoblasts Test 2. Effect on TAZ Activity of Inhibiting PPARγ Function 293T cells (ATCC) were placed in the wells of a 48-well plate (1×10⁵ cells/well) and stabilized. Introduced to the cells were PPARγ and TAZ expression vectors together with vectors aP2-luc (adipose fatty acid binding protein 2 promoter linked to luciferase) and pCMVβ Hong et al., *Science* 2005; 309:1074-8]. For observing the effect on transcription activation of the target gene by the PPARγ or TAZ protein expression, aP2-luc reporter gene was also introduced into the cells. For calibration of the introduction efficiency in cells, vector pCMVβ was introduced in cells in same amounts and the β-galactosidase activity was measured to calibrate the luciferase activity.

After 24 hours, the cells were treated with each of the inventive compounds to a concentration of 10 μM and then further cultivated for 24 hours. Proteins of the resulting cells were extracted with a lysis solution comprising NP-40, and thus luciferase activity was measured (Promega, Sunnyvale, Calif., USA).

Increased inhibitory effect on the aP2 promoter activity was analyzed and the results were calculated in percentage term based on the inhibitory effect on the aP2 promoter activity observed for the non-treated cells in a control group. The results are shown in Table 4.

TABLE 3

Effects on stimulating migration of protein TAZ toward nucleus

| Compound No | II | III | IV | V | VI | VII | IX | XI | XII |
|---|---|---|---|---|---|---|---|---|---|
| Expression (%) | 130.30 | 156.83 | 135.25 | 150.56 | 132.42 | 160.30 | 147.45 | 133.70 | 149.46 |

TABLE 4

| Effects on TAZ activity inhibiting PPARγ function | | | | | | | | | | | |
|---|---|---|---|---|---|---|---|---|---|---|---|
| Compound No | II | III | V | VI | VII | VIII | IX | X | XI | XII | XIII |
| Increased inhibition (%) | 43.2 | 64.6 | 32.3 | 51.3 | 46.7 | 69.2 | 22.7 | 57.5 | 83.0 | 69.7 | 39.9 |

It is shown from Table 4 that the inventive compounds exhibit significant inhibitory effects, particularly the compounds of formulas (III), (VIII), (XI), and (XII) exhibit an inhibitory effect of more than 60%. Accordingly, the inventive compounds inhibit PPARγ by binding to TAZ to inhibit the differentiation of PPARγ into adipocytes, and thus they are useful for preventing or treating obesity.

Test 3. Effect on TAZ Activity of Stimulating RUNX2 Function

Introduced in 293T cells were introduced RUNX2 and TAZ expression vector together with 6×OSE-luc (osteocalcin-specific element linked to luciferase, six copies of RUNX2-binding site in the osteocalcin promoter linked to luciferase) [Hong et al., Science 2005; 309:1074-8]. This test was for an evaluation of an activity of the inventive compounds in stimulating the luciferase activity which increases when RUNX2 binds to TAZ.

After 24 hours, the cells were treated with each of the inventive compounds to a concentration of 10 μM and then further cultivated for 24 hours. The procedure of Test 2 was repeated to extract the cell protein, and then reporter gene analysis was conducted to quantify the effect of the inventive compounds on the TAZ activity in stimulating RUNX2. For comparing the transformation efficaciency, β-galactosidase expression vector (pCMVβ) was introduced to 293T cells and the β-galactosidase activity was measured for calibration.

The osteocalcin promoter activity was analyzed in percentage term based on that of non-treated cells in a control group. When the value exceeds 570% of the average increase by protein TAZ, the compound was considered to have an additional stimulating activity. The results are shown in Table 5.

and then confluently cultivated for 48 hours in a 24-well plate ($3\times10^4$ cells/well). 2 μM rosiglitazone, 5 μg/mL insulin, and 1 μM dexamethasone were added thereto to induce adipocyte differentiation.

After 48 hours, the medium was replaced with a DMEM comprising 5 μg/mL insulin and 10% FBS (fatal bovine serum), and 48 hours later, the medium was replaced with a DMEM comprising 10% FBS. Then, the medium was replaced every 48 hours to evaluate adipocyte differentiation. The inventive compounds were each added during the replacement of the medium. After 8 days, the cells were fixed with 10% formalin, and Oil-red O staining was conducted to confirm adipocytes generated in cells.

The result of the staining showed that adipocyte differentiation was inhibited by the inventive compounds, particularly the compounds of formulas (III), (IV), and (XII).

Further, in case of treating at a higher concentration, markedly increased inhibitory effect was observed for the compound of formula (VII).

<4-2> Inducing Effect on Differentiation of C3H10T1/2 Cells Into Osteoblasts

C3H10T1/2 cells (ATCC CCL 226) were diluted in a α-MEM medium comprising 10% FBS, cultivated in a 96-well plate ($1\times10^4$ cells/well) for 48 hours, and the medium was replaced every 48 hours to observe the osteoblast differentiation. On the initiation of differentiation, the medium was treated with 10 μM of each of the inventive compounds.

After 20 days, the cells were fixed with 70% ethanol and stained with an Alizarin red S solution to confirm increased

TABLE 5

| Effects on TAZ activity of stimulating RUNX2 function | | | | | | | | | | | | |
|---|---|---|---|---|---|---|---|---|---|---|---|---|
| Compound No | II | III | IV | V | VI | VII | VIII | IX | X | XI | XII | XIII |
| Activity (%) | 472.6 | 259.4 | 463.2 | 468.2 | 483.4 | 476.4 | 688.0 | 675.8 | 671.6 | 753.6 | 296.1 | 568.8 |

From Table 5, It can be seen that the additional stimulating activity was observed for the inventive compounds, particularly the compounds of formulas (VIII), (IX), (X), and (XI). Accordingly, the inventive compounds facilitate the RUNX2 activity by binding TAZ to stimulate osteoblast differentiation, and thus, they are useful for preventing or treating osteoporosis.

Test 4. Effect on Differentiation Into Adipocytes or Osteoblasts

The activity of the inventive compounds in promoting the differentiation of 3T3-L1 cells and C3H10T1/2 cells into adipocytes and osteoblasts, was evaluated.

<4-1> Inducing Effect on Differentiation of 3T3-L1 Cells Into Adipocytes

3T3-L1 preadipocytes (ATCC CL-173) were dispersed in a DMEM medium comprising 10% FBS (fatal bovine serum, calcium in osteocytes. In the Alizarin red staining test, the degrees of osteoblast differention can be identified by the intensity of red color.

The result of the staining showed that the osteoblast differentiation was stimulated by the inventive compounds, particularly the compounds of formulas (III) and (V).

Accordingly, the inventive compounds are effective for inhibiting adipocyte differentiation and stimulating osteoblast differentiation, and thus they are useful for preventing or treating osteoporosis or obesity.

While the invention has been described with respect to the above specific embodiments, it should be recognized that various modifications and changes may be made to the invention by those skilled in the art which also fall within the scope of the invention as defined by the appended claims.

What is claimed is:

1. A method for treating osteoporosis in a mammal, comprising administering a compound selected from the group consisting of methyl 2-butyl-6-styryl-1-[2'-(1H-tetrazol-5-yl)biphenyl-4-ylmethyl]-1H-benzimidazol-5-carboxylate;
or methyl 2-butyl-5-styryl-1-[2'-(1H-tetrazol-5-yl)biphenyl-4-ylmethyl]-1H-benzimidazol-6-carboxylate, or a pharmaceutical acceptable salt thereof to the mammal in need thereof.

2. A method for treating obesity or hyperlipidemia in a mammal, comprising administering a compound selected from the group consisting of

- {2-butyl-5-dimethoxymethyl-3-[2'-(1H-tetrazol-5-yl)biphenyl-4-ylmethyl]-3H-imidazo[4,5-b]pyridin-6-yl}phenylmethanol;
- 6-bromo-2-butyl-3-{2'-[1-(1-ethoxyethyl)-1H-tetrazol-5-yl]biphenyl-4-ylmethyl}-3H-imidazo[4,5-b]pyridin-5-ylmethyl acetate;
- (2-butyl-5-dimethoxymethyl-3-{2'-[1-(1-ethoxyethyl)-1H-tetrazol-5-yl]biphenyl-4-ylmethyl}-3H-imidazo[4,5-b]pyridin-6-yl)phenylmethanol;
- 6-bromo-2-butyl-3-[2'-(1H-tetrazol-5-yl)biphenyl-4-ylmethyl]-3H-imidazo[4,5-b]pyridin-5-ylmethyl acetate;
- 2-butyl-7-methyl-5-((methylsulfanylmethoxy)methyl)-6-phenyl-3-[2'-(1H-tetrazol-5-yl)biphenyl-4-ylmethyl]-3H-imidazo[4,5-b]pyridine;
- methyl 2-butyl-6-styryl-1-[2'-(1H-tetrazol-5-yl)biphenyl-4-ylmethyl]-1H-benzimidazol-5-carboxylate; and
- methyl 2-butyl-5-styryl-1-[2'-(1H-tetrazol-5-yl)biphenyl-4-ylmethyl]-1H-benzimidazol-6-carboxylate, or a pharmaceutical acceptable salt thereof to the mammal in need thereof.

* * * * *